US006013125A

United States Patent [19]

Quraishi et al.

[11] Patent Number: 6,013,125

[45] Date of Patent: Jan. 11, 2000

[54] INVESTMENT OF POWDERS AND METHOD FOR RAPID PREPARATION OF INVESTMENT MOLDS

[76] Inventors: Mashallah M. Quraishi, 1800 Ridgecrest Cir., SE., Albuquerque, N.Mex. 87108; Anselmo J. Gutierrez, 10143 Furman Ct., NW., Albuquerque, N.Mex. 87113

[21] Appl. No.: 08/712,552

[22] Filed: Sep. 13, 1996

Related U.S. Application Data

[60] Provisional application No. 60/003,716, Sep. 13, 1996.

[51] Int. Cl.[7] .............................. B22C 1/16; B22C 1/08; B28B 7/34; C04B 11/28

[52] U.S. Cl. .............................. 106/38.35; 106/38.23; 106/38.27; 106/38.3; 106/38.51; 106/38.9; 106/779; 106/788

[58] Field of Search .............................. 106/38.35, 38.51, 106/38.9, 779, 788, 38.23, 38.27, 38.3

[56] References Cited

U.S. PATENT DOCUMENTS

| | | | |
|---|---|---|---|
| 1,901,052 | 3/1933 | Dailey | 106/788 |
| 1,953,075 | 4/1934 | Collins | 106/788 |
| 2,102,444 | 12/1937 | Van Allen | 106/788 |
| 2,229,946 | 1/1941 | Van Allen | 106/788 |
| 2,247,588 | 7/1941 | Neiman | 106/788 |
| 2,333,430 | 11/1943 | Lee et al. | 106/788 |
| 2,539,408 | 1/1951 | Ensign et al. | 106/788 |
| 2,758,936 | 8/1956 | Rosenthal et al. | 106/788 |
| 3,042,537 | 7/1962 | Newell et al. | 106/788 |
| 3,429,359 | 2/1969 | Hollingsworth | 164/37 |
| 4,126,651 | 11/1978 | Valentine | 264/25 |
| 4,180,918 | 1/1980 | Ostrowski | 34/13 |
| 4,518,031 | 5/1985 | Yamanishi et al. | 164/526 |
| 5,026,428 | 6/1991 | Cook | 106/788 |
| 5,183,506 | 2/1993 | Zhang | 106/739 |
| 5,222,543 | 6/1993 | Carlstrom et al. | 164/114 |

FOREIGN PATENT DOCUMENTS

| | | | |
|---|---|---|---|
| 2110058 | 9/1972 | Germany | 106/788 |
| 893933 | 12/1981 | U.S.S.R. | 106/788 |

OTHER PUBLICATIONS

Practical Casting by Tim McCreight, 1986 no month, pp. 20–41, Brynmorgen Press, U.S.A.

The Santa Fe Symposium, by Eddie Bell, Forward and pp. 356–383, Met–Chem Research, Inc., U.S.A. (1990) no month.

“R&R Ultravest”, p. 279 from jewelry manufacturing sales catalogue, (source unknown) (No date).

Chemical Abstract No. 117:75280 which is an abstract of Japanese Patent Specification No. 04–089341 (Mar. 1992).

Chemical Abstract No. 119:78404 which is an abstract of Chinese Patent Specification No. 1066438 (Nov. 1992).

Chemical Abstract No. 125:228995 which is an abstract of Japanese Patent Specification No. 08–183649 (Jul. 1996).

WPIDS Abstract No. 91:1373133 which is an abstract of Japanese Patent Specification No. 03–075253 (Mar. 1992).

WPIDS Abstract No. 91:215625 which is an abstract of Canadian Patent Specification No. 2002994 (May 1991).

*Primary Examiner*—Anthony Green

*Attorney, Agent, or Firm*—DeWitt M. Morgan, Esq.; Kevin Lynn Wildenstein, Esq.; Michelle L. Johnson, Esq.

[57] ABSTRACT

The present invention relates to improved investment powders for use in making improved investment molds for casting metals, and the use of such molds with vacuum and/or either conventional, convection conduction or microwave heating apparatus, to rapidly eliminate water, wax and residual carbon from the mold cavities at temperatures lower than the casting temperature range of the mold at the time of casting.

11 Claims, 16 Drawing Sheets

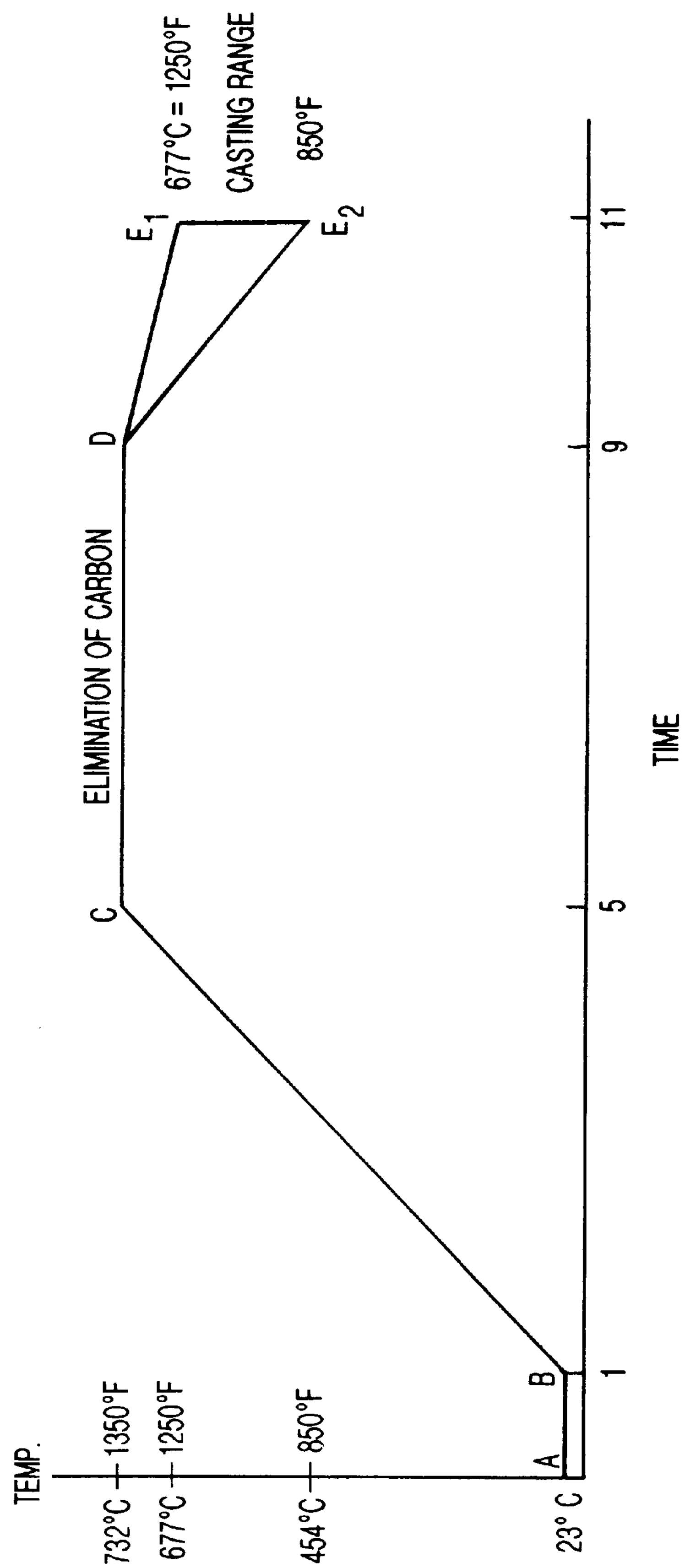
FIG-3
(CONVENTIONAL)

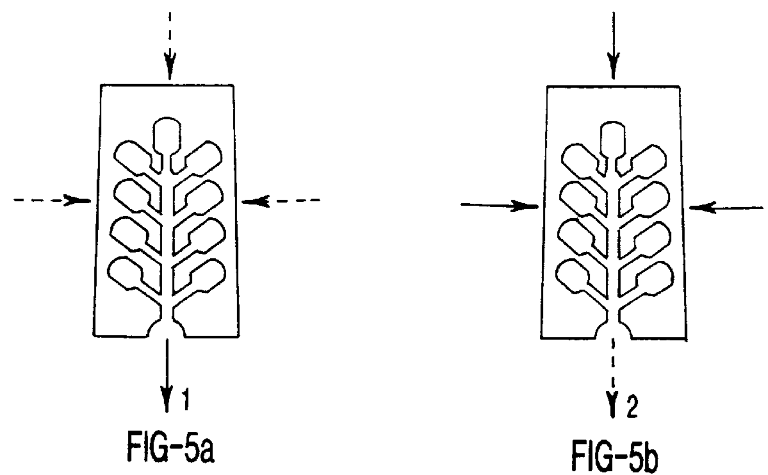
FIG-5a
FIG-5b
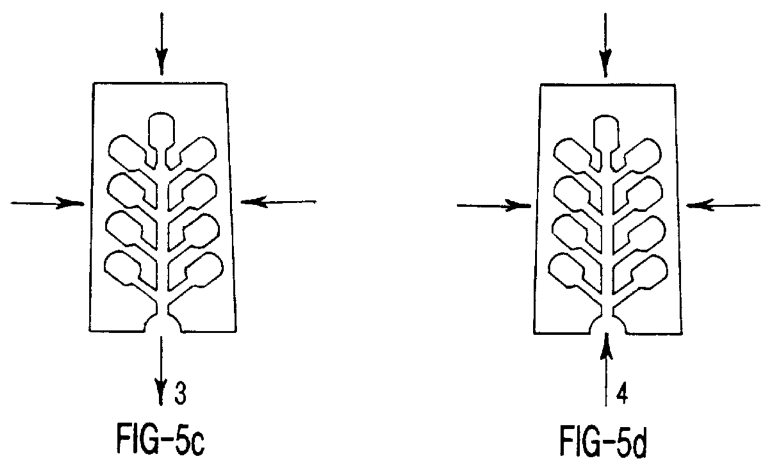
FIG-5c
FIG-5d
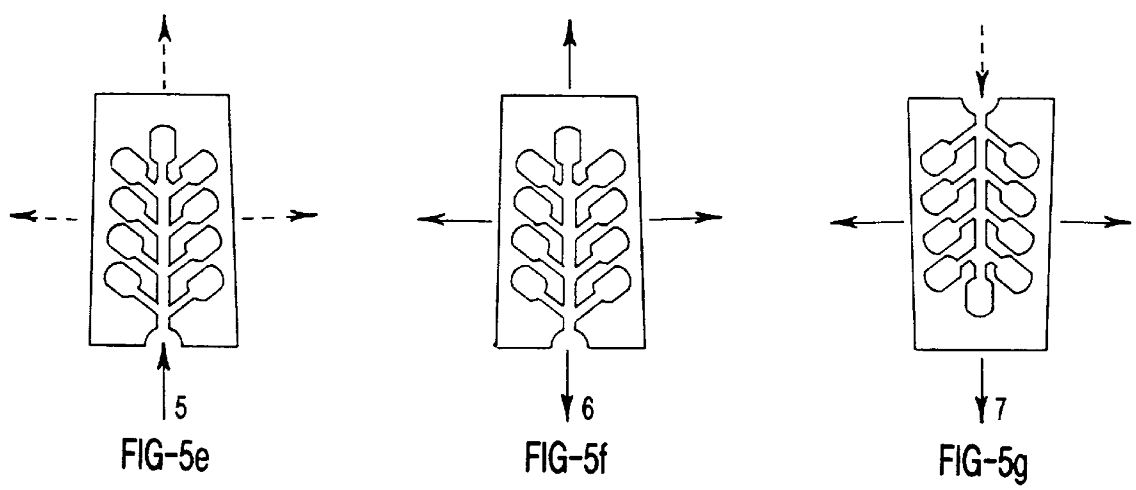
FIG-5e
FIG-5f
FIG-5g

INVESTMENT OF POWDERS AND METHOD FOR RAPID PREPARATION OF INVESTMENT MOLDS

RELATED APPLICATIONS

This application claims the benefit of U.S. Provisional application Ser. No. 60/003716 filed on Sep. 13, 1995.

FIELD OF THE INVENTION

The present invention relates to improved investment powders (with and without silicates) for use in making improved investment molds for casting metals, and the use of such molds in conjunction with vacuum and/or either conventional kiln or furnace, or microwave heating apparatus, to rapidly cure, dehydrate and eliminate the wax (and residual carbon from such wax) from the mold cavity(s) at temperatures lower than the casting temperature range of the mold at the time of casting.

BACKGROUND OF THE INVENTION

The name "lost-wax" casting owes its origin to the fact that an expendable wax pattern of the article (e.g. jewelry) to be cast was first made in wax. This is pattern was fastened to a conical wax sprue rod and then encased in a mold of plaster of paris or some other refractory material. An opening is left in the mold so that most of the wax, when melted, could drain away. The residual wax is then burned away by heating the mold slowly in a kiln at prescribed temperatures for prescribed periods of time. When the wax melted and burned away, the cavity is left in the mold. Molten metal was then poured into the cavity of the mold through the same opening that is used to eliminate the wax, and upon solidification, it assumes the shape of the cavity. After cooling, the mold is broken open to free the casting.

Wax trees (i.e., wax patterns and the sprue to which they are attached) are usually formed from several materials which can be combined, including natural wax, synthetic wax, resins (such as damar, balsam, gum, shellac and rosin, plastic compounds, fillers (such as talc, starch, chalk, soapstone, pumice and wood flour) or even polymeric foam as disclosed by U.S. Pat. No. 2,830,3443. Regardless of the specific composition, the materials employed as the wax tree must be made of materials which will melt, burn and vaporize completely and leave little or no residue in the mold structure. Some plastics don't melt, but burn and vaporize completely leaving no residue.

As seen in FIG. 1*a*, 1*d* and 1*e*, wax tree 13 is attached to sprue base 17, enclosed in a flask 16, typically of metal (e.g. stainless steel; perforated or non-perforated; with or without a flange; tapered or non-tapered; and then surrounded with a heat-resisting plaster compound, typically referred to as investment, 11 in order to form the mold for the metal casting.

Typically, the investment is composed of cristobalite, gypsum, silicas, and modifying agents. Cristobalite is a mineral of volcanic origin. It is now made by heating silicas to 2680° to 3040° F. (1471° to 1671° C.). The cristobalite is an expanding and contracting form of silica which permits the mold to expand without cracking when it is heated and the very hot molten metal is poured into it. Gypsum chemically is hydrated calcium sulphate $(CaSO_4)+2H_2O$. When gypsum is heated gently it becomes Plaster of Paris $(CaSO_4)_2+\frac{1}{2}H_2O$. Gypsum acts as a binder, that is, it rigidly holds all the ingredients in the investment together. Silica is a refractory material. It is infusible, that is, it is not melted or changed by the hot metals cast into it. Silicon dioxide ($SiO_2$), one form of which is finely crushed ordinary beach sand, is used as a silica. The silica cushions or stabilizes the investment while it is being heated during burnout and when it is being cooled just prior to casting. Modifying agents are minerals (copper powder or carbon) in the mixture which produce a reducing (checks oxidation) effect in investment. Modifying agents also include wetting agents (that increase the ability of the investment to flow over the wax tree), chemicals that control the setting time, and debubblizing agents (to assist in removing air from the slurry). The investment powder also must not contain any corrosive or acid producing ingredients which would damage the furnace, flasks or castings. The investment material must be able to be removed quickly and easily from the flask and castings after the metal has been cast into it. Roma-Vest, Kerr Satin Cast and R & R Ultra-Vest are three investments now on the market that are used by jewelers and sold by casting supply houses.

The mixture of investment powder with water is a slurry. The proportion of water to investment powder must be controlled accurately, especially by commercial casters in order to obtain uniform usable castings. Too much water will result in a weak mold. Too much investment powder will make the mold surfaces too coarse and important details in the wax pattern will be lost. All investment manufacturers specify the water-powder investment ratio that should be used with their product. Their recommendations are similar and approximate the following average for jewelry casting: weight of water =40% weight of investment (e.g. 40 parts by weight of water to 100 parts by weight of powder). For very fine, intricate castings, slightly more water (up to 2%) can be added to the investment powder in order to obtain a finer slurry that would flow into smaller crevices more smoothly. For heavier castings, slightly less water (2%) is used with the investment powder in order to obtain a slightly less fluid slurry that would be sturdier for heavier castings.

As those skilled in the art know, the working time of slurries made with commercial investment powders is approximately 8–9 minutes. Setting time is usually 12–14 minutes. The working time of the investment process starts as soon as the investment powder is added to the water and ends when the flask is totally filled (i.e., capped) with investment slurry and left undisturbed to harden. Working time involves 2–4 minutes of mechanical mixing of the investment powder with the water (and not the other way around as it creates lumps and is very hard to mix) at moderate speed in a bowl. The slurry in the mixing bowl is then placed under a bell jar until the investment slurry rises and collapses in the mixing bowl. Typically, a vacuum of 23–27" Hg is pulled. This takes 30–45 seconds (1 minute maximum). The vacuum is typically held for another 10 seconds before releasing. The vacuumed slurry is poured into the flask through the side of the flask, gently allowing it to flow around and through the wax tree pattern(s) until the pattern(s) are all covered (½" above the top pattern). Lightly tapping the flask while filling helps reduce the amount of entrapped air which is reintroduced by pouring. The invested flask is then vacuumed under the bell jar for another 1–2 minutes. The trapped air, if not removed, will cling to the wax patterns as small or large air bubbles which will also be surrounded by the investment. This will ruin the castings for the air bubbles will be cast usually as small or large metal balls (nodules) clinging to the castings.

Both the temperature of water and investment should approximate room temperature 70° F.–80° F. (21°–27° C.). Increasing the temperature of water or the investment will accelerate the setting, hence shorten the working time. Conversely, lower temperature of water or investment could affect the quality of the castings. Some people use distilled water to avoid contaminants of ordinary tap water. Commercial retarder like dry citric acid or sodate are sometimes used in very minute percentages. (i.e., 0.03–0.30 gm for every 100 gm of investment powder) to retard the setting time if desired. Retarder's effect on the properties of plaster in regard to initial setting time.

After being invested, flasks must be permitted to set undisturbed to solidify for at least one hour for small flasks (2" dia.) and two hours for larger flasks. After solidification the sprue base is removed from the flask to expose the bottom of the wax sprue itself. The bulk of the wax is then eliminated, the mold dehydrated and the residual wax vaporized, and the carbon from such wax ("wax carbon") burned out by heating the flasks in a kiln or furnace to 1300° F. to 1400° F. (704° C. to 788° C.). Many casters now use a steam dewaxer, which removes approximately 90% of the wax before burnout.

Molds can be stored for many days before burnout, providing they remain moist. However, if the investment in the flasks becomes dry from being in a dry room for several days, the flasks should be placed in water for a few minutes or better yet, to avoid damaging the mold, they should be wrapped in wet towels to absorb moisture slowly. The investment should be heated only when wet, for dry investments tend to crack when heated. If the mold is heated dry, it can act as a sponge and draw the wax into its pores. Also, water in the wet molds turns to steam when heated and the steam helps in eliminating the wax from the walls of pattern cavities in the mold.

As seen in FIG. 2*a*, after mixture 11 is created as described above, it is inserted into an oven 25, such as a conventional oven, and held at a number of different temperatures above the wax melting point for a long period of time. This process is generally referred to as "burn out" because it is during this time frame that the wax tree is eliminated (or "lost"). The wax melts and disgorges out through sprue opening 10, the mixture 11 is cured into mold 21 as water is vaporized from the mixture, the carbon from the wax is burned off from cured mold 21, and finally, the mold is heated to a proper casting temperature. This period of time can vary depending on the size and shape of the mold, the type of tree being eliminated and the size and shape of the flask. For example, as seen in FIG. 3, for a conventional 4 inch diameter by 8 inch high mold, the time to vaporize water and burn the wax is approximately five hours, and requires the oven temperature to reach 732° C. (1350° F.). Carbon must then be eliminated from the mold at this high temperature for approximately 4 hours. Finally, the mold must be allowed to cool down to the casting temperature of the metal being cast, which can take more than 2 hours depending on the metal alloy being used. While FIG. 3 demonstrates that conventional investment cast processing for small projects takes up to 11 hours, those skilled in the art realize that investment casting usually takes more than 11 hours for larger cast products.

Preferably, as seen in FIG. 2*a*, the mold is positioned in an elevated location in oven 25 by any conventional thermal pad 23, such that as the heat is applied and the wax reaches its melting point, it runs out of the mold to create sprue hole 10. As disclosed in U.S. Pat. No. 3,847,202 to Vaughn, melted wax can be captured for future use, or as disclosed in U.S. Pat. No. 4,854,368 to Vezerian, distilled foam can be vacuum evaporated prior to pouring the alloy into the completed mold. Complete burnout is usually indicated by the disappearance of the sooty black stain around the mouth of the sprue hole. When the stain is gone, the residue has been vaporized. When the mold is fully cured, it is generally allowed to cool to about 260° C. (500° C.) less than the melting point of the metal being cast. At this point the mold should be completely dry, otherwise any moisture will turn to steam as molten metal contacts the mold and creates defects in the casting. In many cases, the presence of moisture may also cause the hot metal to disgorge out of the cavity, making it dangerous for the operator.

In a typical burnout cycle the flasks are heated slowly in a kiln to 400° F. (204° C.) so that the water as moisture turns to steam at 212° F. (100° C.) and can escape through the pores of the mold. Water that is chemically combined with some of the chemicals in the investment powder as water of hydration will be driven off at approximately 375° F. (191° C.). If heated very quickly in the initial stages, vapor pressure could cause cracks in the mold, and the escaping steam, in addition to the vapor pressure along with the thermally expanding wax in the cavities, could break the thin investment walls (dividers) between the wax patterns or in the intricate wax pattern itself (especially when the mold is dewaxed and dehydrated simultaneously in a kiln) resulting in damaged castings.

At 200° F. to 300° F. (93° C.–149° C.), most of the wax (if not earlier removed by steam) immediately melts and flows out through the sprue opening. The steam from the water in the heated moist investment helps to push the wax off the walls of the pattern cavities in the investment. Wax which does not flow out turns to carbon (a black powder) at 1000° F. (538° C.). This carbon is almost completely eliminated between 1300° F. and 1400° F. (704° C. and 788° C.) by combining with oxygen of the air (the furnace or kiln must be ventilated) forming carbon monoxide (CO) and carbon dioxide ($CO_2$). The gases escape through the sprue opening and also through the pores of the mold. All that is left in the mold cavity is ash (i.e., microscopic trace residue). This residue is comprised of trace metals, salts, silicas, and other inorganic elements. Typically, its value should be no more than 0.015% by weight because waxes with a high ash content can cause porosity and inclusions in a casting.

The furnace temperature will rise faster (be hotter) than the temperature of the wet investment in the center of the flask. The difference in temperature can be more than 100° F. (38° C.). To permit the furnace temperature and flask temperature to equalize, the furnace temperature should be held for at least ½ hour for small molds and up to 3 hours for larger molds. Doing so permits the molds to have a uniform temperature throughout.

If the flask is heated over 1500° F. (816° C.), the gypsum binder (calcium sulphate, $CaSO_4 + \frac{1}{2}H_2O$) begins to break down into sulfur dioxide ($SO_2$) and sulfur trioxide ($SO_3$) and, if a casting is poured over 1500° F. (816° C.), these gases will discolor (form sulfides with) the cast metals and stain the metal. Not only will the resulting casting be dark, but the sulphide layer can be so deeply and firmly bonded to the metal that it cannot be removed. This breakdown can also be accompanied by a loss of detail in the mold wall and could also cause metal porosity.

On page 73, in "Centrifugal or Lost Wax Casting" by M. Bovin and P. M. Bovin (14th Printing, 1992) the following burn-out cycles were recommended:

| 5 Hour Cycle | 8 Hour Cycle | 12 Hour Cycle |
| --- | --- | --- |
| For flasks up to 2½" × 2½" preheat furnace to 300° F. (149° C.) | For flasks up to 3½" × 4" preheat furnace to 300° F. (149° C.) | For flasks up to 4" × 8" preheat furnace to 300° F. (149° C.) |
| 1 hour - 300° F. (149° C.) | 2 hour - 300° F. (149° C.) | 2 hour - 300° F. (149° C.) |
| 1 hour - 700° F. (371° C.) | 2 hour - 700° F. (371° C.) | 2 hour - 600° F. (316° C.) |
| 2 hour - 1350° F. (732° C.) | 3 hour - 1350° F. (732° C.) | 2 hour - 900° F. (482° C.) |
| 1 hour - See note | 1 hour - See note | 4 hour - 1350° F. (732° C.) |
| | | 2 hour - See note |

In Bovin & Bovin (supra) at page 73 the following investment casting temperatures are recommended:

| | |
| --- | --- |
| White Gold | |
| Thin objects | 1050° F.–1150° F. (566° C.–621° C.) |
| Thick objects | 900° F.–1000° F. (482° C.–538° C.) |
| Yellow Gold | |
| Filigree | 1050° F.–1150° F. (566° C.–621° C.) |
| Thin objects | 900° F.–1000° F. (482° C.–538° C.) |
| Thick objects | 800° F.–850° F. (427° C.–454° C.) |
| Silver, Brass | 800° F.–850° F. (427° C.–454° C.) |
| Bronze | 900° F. (482°°C.) |

It is also typically recommended that the furnace temperature should be held at the desired investment casting temperature for at least ½ hour to permit the investment temperature to drop to the furnace temperature.

The foregoing procedure is generally represented by FIG. 3 in which:

A represents the point where the flask was just poured or invested, and then set aside undisturbed to let the invested flask (mixed, vacuumed slurry) to set;

A-B represents the minimum time (1 hour) for allowing a mold to set before it could be processed for steam dewaxing or heated slowly for simultaneous dewaxing and dehydrating. Normal setting or hardening of mold requires 1–2 hours;

B-C represents the slow rise in the temperature of the mold to 1350° F. (732° C.) whether the mold was dewaxed in a steamer for 1 hour or it was directly put in the kiln for dewaxing and dehydrating simultaneously. During this time the wax that didn't drip out through the mouth of the main sprue, and was left entrapped in the cavities of the mold, or the wax that has penetrated into the walls of the mold due to its thermally expanding nature, turns to wax carbon at around 1000° F. (538° C.);

C-D represents the time at which the mold is held at 1350° F. (732° C.) for several hours to essentially eliminate the wax carbon from the mold cavity;

D-$E_1$/$E_2$- the gradual dropping of the mold temperature to the desired casting temperature (typically 850–1250° F. (454–677° C.)).

Molds at this stage are fragile and should be handled with care. Dropping or bumping can break thin investment dividers within the cavities. Also, uneven heating of the mold during the foregoing process can cause cracks in the mold, which will result in bad castings.

The foregoing process, while still the standard process in many industries, has a number of drawbacks both from the standpoint of the investment powders used and the process.

Several problems exist with the typical investment powder used for casting gold, silver, brass and bronze alloys (e.g., 25–40% gypsum and 75–60% silica (various forms), with small percentages of modifiers (as indicated above)). For example, this type of investment powder can be hazardous to the user, as silica compounds are known to cause respiratory problems. Secondly, because silica is a dielectric material, it does not suscept to microwave energy (which is important for the reasons set forth with regard to one of the preferred embodiments of the invention). Further, because silica is also a refractory material, heating by conduction is time-consuming. Moreover, molds produced from this investment powder are structurally weak and typically cannot be used in flaskless applications. Finally, molds made from such powders cannot withstand rapid thermal shock and temperature differentials during any phase of the casting process as they crack easily.

In addition to the foregoing, molds made with typical investment powder should not be heated much above 1350° F. (732° C.). As already mentioned, if the mold is heated over 1500° F. (816° C.), the gypsum binder ($CaSO_4$+½$H_2O$) begins to break down into sulphur dioxide ($SO_2$) and sulphur trioxide ($SO_3$). $CaSO_4$ is sensitive to high temperature. At about 1200° C. (2192° F.), thermal decomposition results in the formation of calcium oxide, sulphur dioxide and oxygen, and, possibly, sulphur trioxide.

$$2CaSO_4 \rightarrow 2CaO+2SO_2+O_2$$

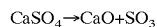

The addition of silica ($SiO_2$) to calcium sulphate lowers the temperature of decomposition to 1000° C. (1832° F.), producing:

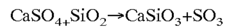

The foregoing breakdown can also result in a loss of detail in the mold walls. Thus, conventional $CaSO_4$ bonded investment powders cannot be used to cast platinum or palladium. Platinum has a melting point of 3225° F. (1773° C.); palladium, 2831° F. (1555° C.). Instead, platinum/palladium investment casting requires a mold capable of heating to extremely high temperatures (i.e., 1600° F. (871° C.)), like a phosphate bonded investment binder.

Further, since the resultant mold is very hard and has very little porosity and since platinum and palladium chill quickly (because of their high melting points) high torque, centrifugal casting equipment is required. Finally, because of the differences between investment powders used for platinum, it is very difficult to remove the casting from the mold. Hammer and chisel techniques are required, as such molds will not break up/or dissolve when immersed in water, while molds used for gold and silver will.

There are a number of disadvantages to the conventional heating process generally described above:

1. Heat losses occur due to the furnace being fluted and ventilated.

2. Molds cannot be enclosed in a heat shield in this system, hence they cannot be prevented from radiating heat away.

3. Molds are heated by conduction from exterior of the mold to the interior, which takes a long time to get a uniform temperature.

4. The mold takes several hours to combust carbon at 1350° F. (732° C.) because it uses the $O_2$ of the outside air.

5. The mold has to be heated to 1350° F. (732° C.) for elimination of carbon and then dropped to casting temperature which consumes additional time and energy.

The times, temperatures and heat losses involved demonstrate the extensive amount of energy used in the process.

Additionally, the mold is capable of cracking if the process is not carefully monitored and controlled. Further, as the wax is heated, it thermally expands prior to melting and eventually decomposing, and may apply force to or penetrate the mold composition which may generate fluid pressure and gases within the mold thereby causing it to crack. If the mold is cracked, the resulting cast product reflects this flaw and, thus, may not be usable commercially.

The above described process presents additional problems when casting with precious or semi-precious gems. As described in the *American Jewelry Manufacturer*, June 1993, gems can be processed in wax and cast which results in cost savings. However, when gems are processed in an investment casting, extra care must be taken during the burn out phase to protect the structure, beauty and luster of the gems as they are heated to very high temperatures for a very long period of time. It is generally recommended that when casting with gems, one should use lower burnout temperatures (e.g., lower than 427° C. (801° F.)) for, approximately, 14 hours in order to protect the gems. To prevent the gems from being damaged or destroyed, the temperature should never exceed 454° C. (849° F.). Further, it is recommended that alloys be used which flow more easily at lower temperatures than typically used for investment casting. Even if these procedures are followed, only certain gems can be processed (e.g. diamond, ruby, sapphire, garnet and cubic zirconium). Certain gems are not recommended for investment casting under any circumstances, including amethyst, aquamarine, coral, jade, lapis, opal, pearl, peridot, topaz, tourmaline and turquoise.

Applicants are aware of a number of patents which disclose the use of microwaves in conjunction with investment casting: U.S. Pat. No. 4,655,276 to C. R. Bird, et al; U.S. Pat. No. 4,126,651 to J. M. Valentine; U.S. Pat. No. 4,180,918 to R. C. Ostowski; U.S. Pat. No. 4,518,031 to A. Yamanishi, et al; and U.S. Pat. No. 3,847,202 to C. D. Vaughn, et al.

Bird, et al., disclose a form of creating a shell mold containing external layers of microwavable susceptors. Bird, et al. disclose that the wax tree could be introduced into a mold by first dipping the wax tree in a slurry of conventional molding material such as ceramic, and draining the resulting structure. A stucco layer is then applied to the structure and allowed to dry. Then, subsequent layers of slurry containing microwavable susceptors, such as graphite or metal oxides, are applied. This layering process will continue until the mold walls are of sufficient thickness. At this point, the resulting structure is allowed to thoroughly dry. Microwave energy is then applied to the dry mold and to partially reduce the size of the wax tree such that the wax no longer contacts the mold surface. Finally, the mold is fired in a conventional oven to melt the remainder of the wax in order to avoid cracking of the mold.

Bird's disclosure has limited applications. For example, unlike conventional cast molds, shell molds are very thin and incapable of casting delicate and intricate products, especially those found on densely-packed wax trees. Additionally, shell casting is not preferred for casting products having a high quality, non-porous surfaces as the process of dipping necessarily reintroduces air back into the mixture. Because they lack structural strength, shell casts cannot typically retain precious gems. Finally, unlike the present invention, the Bird, et al. disclosure of the use of metal oxides $Fe_2O_4$ (presumably $Fe_3O_4$), $MnO_2$ (presumably MnO), NiO and cobalt oxide (CoO) as susceptors which require heating beyond the desired casting temperature before the susceptors decompose. For example, $FeO_4$ decomposes at 1538° C. (2800° F.), MnO at 1650° C. (3002° F.), $MnO_2$ decomposes at 535° C. (995° F.), NiO at 1990° C. (3614° F.), and cobalt oxide at 1935° C. (3515° F.). None are water soluble.

TABLE 1

| | Melting Point | Soluble in Water |
|---|---|---|
| $Fe_3O_4$ | 1538° C. (2800° F.) (decomposes) | No |
| $Fe_2O_3$ | 1565° C. (2849° F.) | No |
| $MnO_2$ | 535° C. (995° F.) (decomposes) | No |
| MnO | 1650° C. (3002° F.) | No |
| NiO | 1990° C. (3614° F.) | No |
| CoO | 1935° C. (3515° F.) | No |

Another example of the use of microwave heating of gypsum is found in U.S. Pat. No. 4,126,651 to Valentine. This patent discloses using a two-step microwave heating process, wherein a first microwave heating is applied to the investment mold to eliminate water from the mold, and a second microwave heating is applied to the mold to remove the remaining crystallized water.

It is an object of the present invention to provide improved investment powders for use in making improved investment molds for casting metals, wherein water, wax and residual carbon from such investment molds are eliminated when heated by conventional (convection or conduction) ovens or microwave ovens at a temperature less than the casting temperature of the metal.

It is a further object of the present invention to provide an improved investment powder for making molds by adding at least one modifier to conventional investment powders which, when heated, decomposes producing oxygen, which can combust with carbon to form carbon dioxide gas which can be withdrawn from the mold by any conventional means.

It is a further object of the present invention to provide an improved investment powder for making molds by adding at least one suscepting agent to conventional investment powders which, when heated by microwave energy, assists in rapidly heating the mold.

It is also an object of the present invention to provide an new investment powder for making molds by combining preferably gypsum and wollastonite ($CaSiO_3$) which, when mixed with water, results in a stronger mold after it is cured and able to withstand high temperatures for prolonged periods.

It is a further object of the present invention to provide a process for rapidly curing an investment mold containing modifiers and/or suscepting agents throughout the mold wherein after heating for a predetermined time, the mold is set faster; uniformly heated; wax, hydration and carbon are eliminated at a temperature less than the casting temperature of the metal; and mold cracking is minimized or completely eliminated.

It is a further object of the present invention to provide a process for rapidly curing an investment mold containing modifiers and/or suscepting agents throughout the mold wherein the mold has the requisite thermal properties of a conventional casting mold.

It is a further object of the present invention to provide a process for creating a mold containing oxidizing agents which are susceptible to heat radiation, and more particularly, to microwave radiation.

It is a further object of the present invention to provide a process for creating a mold made of modifiers and/or susceptors in order to investment cast in a significantly shorter time period than conventional methods.

The present invention provides several processes and an apparatus for creating a mold having modifiers or susceptors which will allow the processing of investment casting materials to be significantly reduced. Such a process can be applied in various applications and industries, including but not limited to casting of jewelry, toys, metal alloys, automobile parts, dental devices and biomedical devices.

The advantages of the present invention are numerous. First, the present invention requires substantially less power than conventional casting methods. Second, the present invention allows vaporization of wax to occur way below 676°–732° C. (1250°–1350° F.). Finally, and most importantly, the present invention results in substantial time savings over processing of molds using the conventional methods. As those skilled in the art will appreciate, this will result in substantial manufacturing increases and, thus, higher profits.

SUMMARY OF THE INVENTION

The present invention relates to improved investment powders for use in making improved investment molds for casting metals, and the use of such molds with vacuum and/or either conventional, (i.e., convection or conduction) heating, or microwave heating apparatus, to rapidly set the mold, eliminate water, wax and residual carbon from the mold cavities at temperatures lower than the casting temperature range of the mold at the time of casting.

In one embodiment the present invention includes an improved investment powder for making molds for casting metals. This improvement includes the addition of an oxidizing agent to conventional investment powders which, when heated to predetermined temperatures below the casting temperature of the metal used, decomposes releasing oxygen to help combust carbon in the mold cavities. Gases formed during this reaction are withdrawn from the mold by a vacuum or any conventional means. Preferably, the oxidizing agent is a nitrate. The oxidizing agent can also include oxides, chlorates, and peroxides.

Another embodiment of the present invention is a non-silica investment powder for creating molds for casting metals. This new investment powder includes mixing a predetermined amount of gypsum to wollastonite. This chemical combination, when mixed with water, results in a stronger mold after it is cured than conventional powders, and is capable of withstanding very high temperatures to cast metals such as platinum and palladium. To this, limestone, oxidizing agents, modifiers, silicon carbide, and sugar may be added.

In another embodiment the present invention includes adding a suscepting agent to a conventional investment powder that, when microwave energy is applied, is excited enough to generate heat within the mold to assist in the rapid heating of the mold. In one form, sugar is a preferred susceptor.

As another embodiment, the present invention includes the process of preparing a mold for casting a metal by employing any of the investment powders disclosed (including the use of oxidizing agents, modifiers, special modifiers and/or suscepting agents), such that: the mold can be set fast; and, as the mold is heated to a predetermined casting temperature range, water, wax and carbon, are eliminated from the mold's cavities at temperatures less than a predetermined casting temperature range. The mold can then be raised to a predetermined casting temperature without exceeding such casting temperature.

In another embodiment, the present invention includes the use of conventional (i.e., conduction or convection) heating, or microwave energy to heat the molds made from any of the investment powders disclosed to a predetermined casting temperature range, such that the mold is set fast, dehydrated, dewaxed and carbon eliminated at temperatures less than a predetermined casting temperature range. The mold can then be raised to a predetermined casting temperature without exceeding this temperature.

In another embodiment, the present invention includes the use of a vacuum to any of the molds disclosed to assist in the dehydrating, dewaxing and carbon elimination of such a mold.

BRIEF DESCRIPTION OF THE DRAWINGS

FIG. 3 is a time versus temperature graph for preparing a conventional (prior art) mold used in the lost wax investment casting process;

FIGS. 5*a*–5*g* are side views of a cured mold depicting vacuum pressure flow when various types of vacuum pressures are applied;

DESCRIPTION OF THE PREFERRED EMBODIMENTS

Figure 1A:
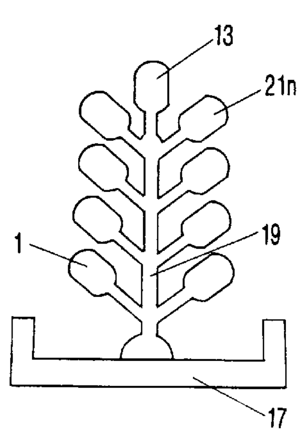
FIG. 1*a* is a side view of a wax tree attached to a rubber base.

The present invention includes a new composition of investment powder that can, either by itself or when mixed with modifier(s) and/or susceptor(s), rapidly conduct heat within the resulting mold in a significantly shorter period than traditional methods in either conventional ovens or microwave ovens. In order to achieve such results, the traditional investment mixture must include chemical compositions which have characteristics that make the resulting mold more conductive to heat generating energy without affecting the desirable characteristics of typical investment powders.

Standard investment powders contain 25–40 percent gypsum ($CaSO_4$) and 60–75 percent silica. To this, one of the preferred embodiments of the present invention includes the addition of a modifier. The determination of the proper modifier depends upon the chemical composition of the investment used (e.g., silica versus nonsilica), but in either case, the modifier must react with the investment powder to retain the same characteristics of the powder while making the resultant admixture more heat conductive.

As set forth in Table 2, preferred modifiers decompose at temperature ranges from 100°–561° C. (212°–1042° F.).

TABLE 2

| Compound | Boiling Pt. Decomposition Temperature (° C.) | Form of Compound | Melt Pt. (° C.) | Water Soluble |
|---|---|---|---|---|
| $KNO_3$ | 400d | Nitrate | 334 | Yes |
| $NaNO_3$ | 380d | Nitrate | 307 | Yes |
| $NaNO_2$ | 320d | Nitrite | 271 | Yes |
| $Ca(NO_3)_2$ | | Nitrate | 561 | Yes |
| $NH_4NO_3$ | 210d | Nitrate | 169.6 | Yes |
| $KMnO_4$ | | Oxide | d < 240 | Yes |
| $KO_2$ | d | Oxide | d380 | Yes |
| $KClO_3$ | 400d | Clorates | 356 | Yes |
| $CaO_2$ | | Peroxide | 275d | Yes |
| $Ca(ClO_3)_2$ | | Clorates | 340 ± 10d | Yes |
| $(CaClO_4)_2$ | | Clorates | 270d | Yes |
| $Ca(ClO)_2$ | | Hypochorite | d100 | Yes |
| $K_2O$ | | Oxide | d350 | Yes |
| $NaClO_3$ | d | Chlorate | 248–261 | Yes |

During decomposition of such oxidizing agents, $O_2$ is released. For example, as heat is applied to a mold containing $KNO_3$, it decomposes to $N_2$, KO, $NO_x$ and $O_2$ by 400° C. (204° F.); while $Ca(NO_3)_2$ decomposes to $N_2$, CaO, $NO_x$ and $O_2$ by 561° C. (1042° F.). The extra oxygen molecules released are then free to react with excess carbon to form carbon dioxide which can easily be removed from the mold by conventional means, such as exhaust or particle vacuuming. Again, for $KNO_3$, the percentage (by weight of the investment powder) is ½–10%, preferably ½–3%. For [Ca $(NO_3)_2$ the percentage (again by weight of the investment powder) is ½–10%, preferably ½–2½%. In addition to single use, two modifiers (e.g. $KNO_3$ and $Ca(NO_3)_2$) can be used in the same investment powder.

As a summary, the following water soluble oxidizing agents can be used in the investment powder of the present invention: $KNO_3$, $Ca(NO_3)_2$, $LiNO_3$, $Fe(NO_3)_2$, $NaNO_2$, $Ni(NO_3)_2$, $Cu(NO_3)_2$, $Al(NO_3)_2$, $NH_4NO_3$ and $Mg(NO_3)_2$. The percentages used of the oxidizing agents, wollastonite, and gypsum need not be exact, but can be approximate.

EXAMPLE 1

To demonstorate the effect of ½% $KNO_3$ and 2½% $Ca(NO_3)_2$ on the properties of the gypsum binder of the conventional investment powder with conventional (non-microwave) setting and conventional kiln.

Procedure (1) 40 lbs. =18143.60 gm of "Prevest" brand conventional investment powder (approximately 30% $CaSO_4$; 70% silica) was used for an 8" perforated stainless flask (3.5"×9").

(2) 18143.60 gm ×0.39 =7076 ml of $H_2O$ (39%) tap water at about 75° F. (24° C.) temperature before mixing.

(3) ½% $KNO_3$ (18143.60 ×0.005 =90.72 gm of $KNO_3$ 2½% $Ca(NO_3)_2$ (18143.60 ×0.025 =453.6 gm of $Ca(NO_3)_2$).

(4) No retarder (e.g. citric acid) was used.

(5) Working time was 5 minutes; setting time 7–8 minutes. All the flask with wax tree were invested in an investing machine (temperature of the mix was cold).

(6) Setting: The molds were allowed to set for 2 hours. No water separation. The molds were hard to fingernail pressure at the end of 2 hours.

(7) Dewaxing was done in the steamer for 1 hour.

(8) Burn out in a gas kiln:

1 hour @ 400° F. (204° C.)

1 hour @ 800° F. (427° C.)

2 hours @ 1050° F. (566° C.)

Carbon was eliminated (9) The flask were casted with sterling silver with the help of a conventional induction vacuum casting machine.

(10) Results: Complete castings with very slight flaws (i.e., very minute surface imperfections on some castings.)

(11) Observation: The molds were strong, they didn't crack, and carbon elimination was successfully done by 1050° F. (566° C.). The mold breaks away by hammering the flask.

(12) Conclusion: ½% $KNO_3$ and 2½% $Ca(NO_3)_2$ affected the gypsum binder of the conventional investment powder by accelerating its setting time thereby shortening its working time (normal working time is 8–9 minutes for conventional investment powder without any modifiers) but didn't affect negatively its setting strength as the molds were strong and didn't crack when they were heated.

EXAMPLE 2

To demonstrate the effect of 3% $Ca(NO_3)_2$ on the properties of conventional gypsum binder of the conventional powder.

Procedure (1) 40 lbs. =18143.60 gm of conventional investment powder was used to invest 8 perforated metal flask (4"×8").

(2) 18143.60 gm ×0.40 =7257.44 ml of $H_2O$ (40%) tap water used at about 74° F. (24° C.) temperature before it was mixed.

(3) 3% of $Ca(NO_3)_2$ (18143.60 gm ×0.03 =544.31 gm).

(4) No retarder was used.

(5) Working time was 7–7½ minutes. All the flask with wax tree was invested in an investing machine. Setting time 9–10 minutes.

(6) Setting: The molds were allowed to set for 2 hours at room temperature. Molds were quite hard to fingernail pressure.

(7) Dewaxing was done in the steamer for 1 hour. From visual inspection they looked wax-free.

(8) Burn out in a gas kiln:

2 hours @ 400° F. (204° C.)

2 hours @ 850° F. (454° C.)

2 hours @ 1150° F. (621° C.)

Carbon was eliminated completely. All the flasks were casted with sterling silver by the help of an induction vacuum casting machine.

(9) Results: Complete castings with very, very slight surface imperfections on castings.

(10) Observation: The molds were slightly hard but broke easily by hammering the flask. Carbon elimination was good. The cast pieces had a bright satin surface.

(11) Conclusion: The setting strength of the conventional investment powder was not affected by the 3% of $Ca(NO_3)_2$. Just the working time had been shortened a little bit.

EXAMPLE 3

To demonstrate the effect of 2% $KNO_3$ and 7% of $Ca(NO_3)_2$ on the properties of the gypsum binder of the conventional investment powder.

Procedure (1) 40 lbs. =18143.60 gm of conventional investment powder was used to invest 8 perforated metal flasks (4"×8").

(2) 18143.60 gm ×0.40 =7257.44 ml of $H_2O$ (40%) tap water at about 74° F. (24° C.) temperature before it was mixed.

(3) 2% of $KNO_3$ (18143.60 gm ×0.02 =362.9 gm); 7% of $CaNO_3$ (18143.60 gm ×0.07 =1270.052 gm).

(4) Retarder: dry citric acid 0.005% (18143.6 gm× 0.005=90.7 gm).

(5) Working time was 12–13 minutes. All the flasks with wax trees were invested in an investing machine. Setting time 15 minutes.

(6) Setting: The molds were allowed to set for 2 hours at room temperature. Molds were slightly soft to fingernail pressure, but looked good.

(7) Dewaxing was done in the steamer for 1 hour. They looked clean and wax free.

(8) Burn out in a gas kiln:

2 hours @ 400° F. (204° C.)

1 hour @ 850° F. (454° C.)

2 hours @ 1050° F. (566° C.)

Carbon was eliminated completely. All the flasks were casted with sterling silver by the help of an induction vacuum casting machine.

(9) Results: Complete castings with very slight surface imperfections on some castings.

(10) Observation: The molds were slightly soft to fingernail pressure when they were set, but didn't have any cracks when they were heated. Carbon elimination was very good. The cast pieces had bright satin surfaces.

(11) Conclusion: The setting strength of the conventional investment powder was affected either by the percentages of the modifiers or the percentages of the retarder.

EXAMPLE 4

To demonstrate the effect of 7% of $KNO_3$ on the properties of the gypsum binder of conventional investment powders.

(1) 40 lbs. =18143.60 gm of conventional investment powder, sufficient to invest 8 perforated flasks (4"×8") (flask stainless steel).

(2) 18143.60 gm ×0.40 =7257.44 ml of $H_2O$ (40%) tap water at about 74° F. (24° C.) temperature before it was mixed.

(3) 7% $KNO_3$ (18143.60 gm ×0.07 =1270.052 gm of $KNO_3$).

(4) Retarder: 0.005% of dry citric acid (18143.6 gm ×0.005=90.7 gm).

(5) Working time was only 5½–6 minutes, all the flasks (with wax tree) were invested in an investing machine which mixes in vacuum and pours in vacuum. Temperature of the mix was cold (56° F. (13° C.)). Setting time is 8–10 minutes.

(6) Setting: The molds were allowed to set at room temperature for 1–18 hours. Even then they were found wet. Some water had separated from the mold and the molds were found soft to fingernail pressure.

(7) Dewaxing was done in the steamer for 1¼ hour, but they didn't appear as though they were dewaxed well.

(8) Burn out in a gas kiln:

1 hour @ 400° F. (204° C.)

1 hour @ 850° F. (454° C.)

Carbon was not eliminated, but instead wax was burning at this stage indicating that the molds were not dewaxed well.

Another 3 hours @ 850° F. (454° C.)

Yet the carbon was still not completely eliminated. Raised kiln temperature.

2 hours @ 1250° F. (677° C.)

All flasks were cast with sterling silver by the help of an induction vacuum casting machine.

(9) Results: Incomplete casting with surface imperfections. Note: These molds were not quenched in water, but were broken out by hammering the flask.

(10) Observation: The molds had cracks, portions of the molds within the cavities had blocked the gating to the main sprue, hence carbon couldn't be completely eliminated.

(11) Conclusion: 7% of $KN\mathbf{0}_3$ affected the gypsum binder of the conventional investment powder by weakening its setting strength. Breakdown of investment molds.

EXAMPLE 4a

To demonstrate the effect of 5% $KNO_3$ on the properties of the gypsum binder of the conventional investment powder, Example 4 was repeated, except the percent of $KNO_3$ was reduced by 2%. Conclusion: even 5% of $KNO_3$ affected the gypsum binder of the conventional investment powder by weakening its setting (or green) strength.

Figure 4:
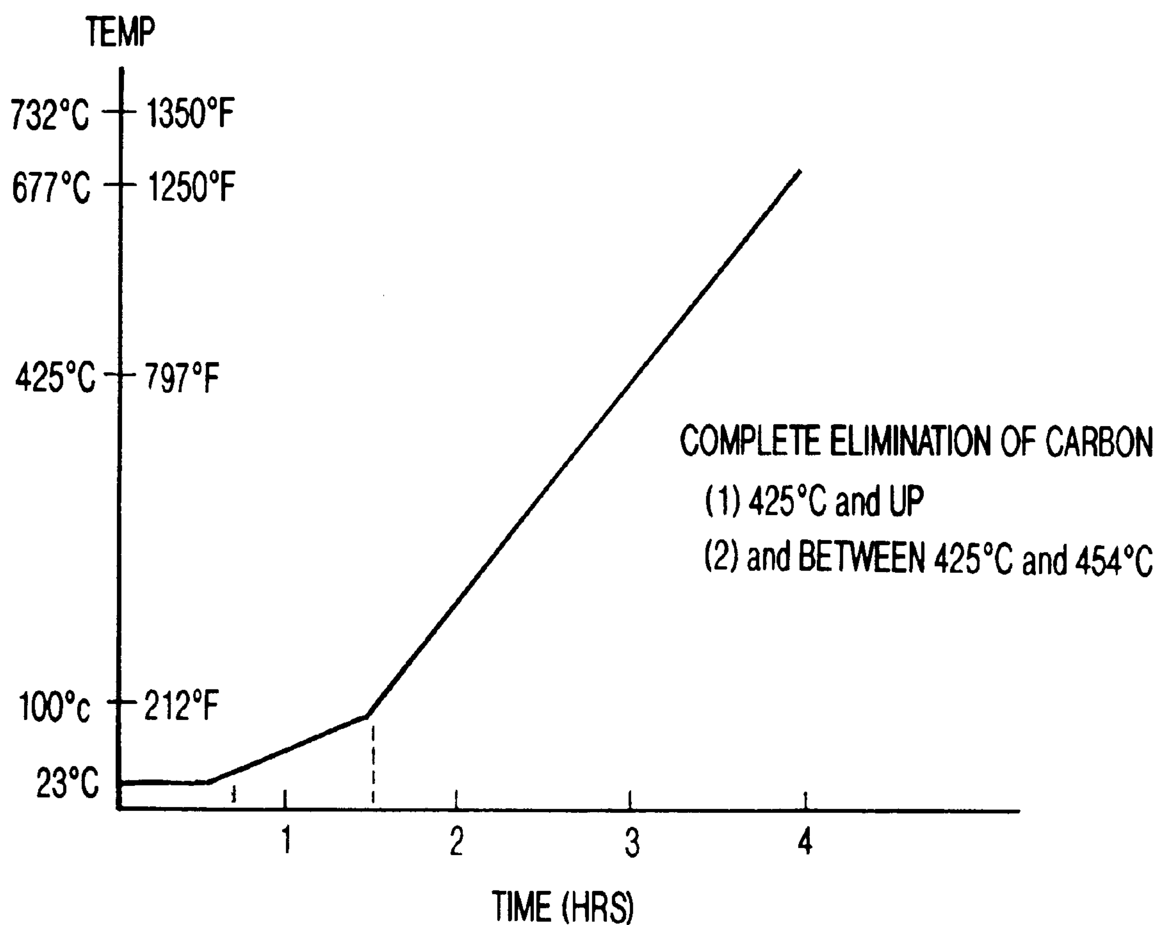
FIG. 4 is a time versus temperature graph when an investment mold with modifiers is prepared according to the present invention and heated in a conventional oven or kiln.

With reference to FIG. 3, those skilled in the art will understand that under conventional burnout methods, the time to completely burn off carbon from a mold takes approximately 8 hours and requires that the mold reach a temperature of at least 732° C. (1350° F.). In contrast, as seen from FIG. 4, with a conventional oven or kiln the addition of the modifiers (one or more) of the present invention drastically reduces the setting, dehydration, dewaxing and the burn out time of the mold (to approximately ⅓ the time of prior conventional methods), and at a much lower temperature (1250° F. (677° C.) versus the prior 1350° F. (732° C.)) due to the rapid removal of carbon. Dehydration, dewaxing and elimination of the water of evaporation from the mold will occur within 1–2 hours at a mold temperature of 100° C. (212° F.) and upto 150° C. (302° F.) and carbon burnout will occur within 3–4 hours at a mold temperature range of 425°–454° C. (797°–849° F.).

Moreover, because the carbon is already eliminated, the temperature of the mold can be raised directly to casting temperature (e.g. 677° C. (1250° F.)) without the need to exceed this temperature (i.e., 732° C. (1350° F.)). Finally, as those skilled in the art will appreciate, lost wax processing can be accomplished even faster with the addition of a vacuum to the mold, as the vacuum aids in the quicker removal of moisture, gas, vapors, or melted wax.

The present invention's modifiers have several advantages heretofore unknown to the art. For example, oxidizing agents such as $KNO_3$ and $Ca(NO_3)_2$, when mixed with water, create an endothermic reaction wherein heat is absorbed. Thus, as investment powder containing oxidizing agents is mixed with water, a slight temperature drop occurs while the modifiers accelerate the set up time of the mixture. Thus, adding modifiers to traditional investment powders results in faster set up time of the mixture. In another example demonstrating the benefits of the present invention, the decomposition of oxidizing agents allow the released oxygen to react with excessive carbon within the mold to form $C\mathbf{0}_2$. In this fashion, most if not all carbon is eliminated by 454° C. (850° F.).

The advantages of the oxidizing mold are numerous. First, the modifiers in the mold assist in accelerating the setting time of the mold. Second, carbon elimination occurs due to the reaction with oxygen produced by the oxidizing mold. Third, the mold can be cast right after burn out, which is especially useful when casting with gemstones such as diamonds. In traditional methods, for example, casting gems such as diamonds above 454° C. (850° F.) may result in noticeable, but adverse, effects to the diamond. Finally, the time for heating an oxidizing mold is significantly reduced compared to the conventional casting process. Therefore, with the addition of modifiers to any form of investment powder, including those disclosed in the present invention, casters and foundry operators are now able to create a mold which will achieve burn out much faster than traditional methods and at much lower temperatures.

The selection of proper oxidizing agents depends upon several factors. First, as heat is applied, the agents must decompose to release sufficient oxygen which can readily react with carbon in the cavities of the mold. This can be controlled with a predetermined percentage of oxidizing agent added to the investment powder. Where the percentage of oxidizing agent does not badly affect on the properties of the investment powder, like initial set time, setting expansion, tensile and compressive strength. Second, these agents should be capable of decomposing when any form of heat-producing energy (such as conventional heat, convection heat, or microwave energy) is applied at a predetermined temperature range. Third, the addition of the proper oxidizing agent with conventional investment powder will assist in structurally strengthening the mold in flaskless mold applications while still allowing the mold to break apart after casting. Fourth, despite the release of oxygen into the mold cavity, the agents should not ultimately affect the metals while casting. Finally, oxidizing agents should preferably be susceptible to microwave energy. Some oxidizing agents having these characteristics are seen if Table 2.

Figure 1B:
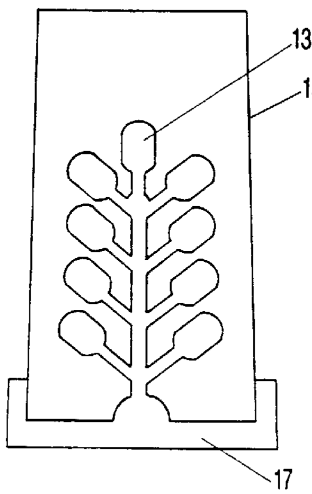
FIG. 1*b* is a side view of the structure in FIG. 1*a* inserted into a plastics flask.
Figure 1C:
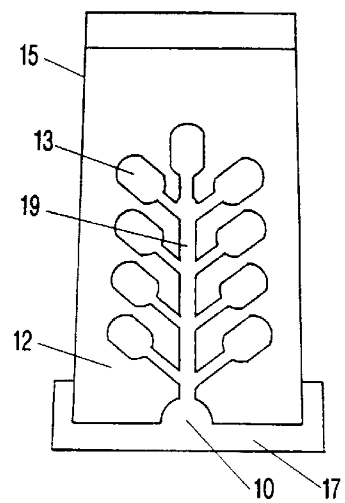
FIG. 1*c* is a side view of the structure in FIG. 1*b* after investment slurry has been poured into the flask.
Figure 1D:
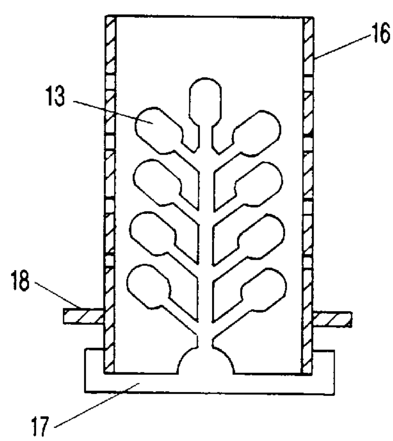
FIG. 1*d* is a side view of the structure in FIG. 1*a* inserted into a perforated metal flask with flange.
Figure 1E:
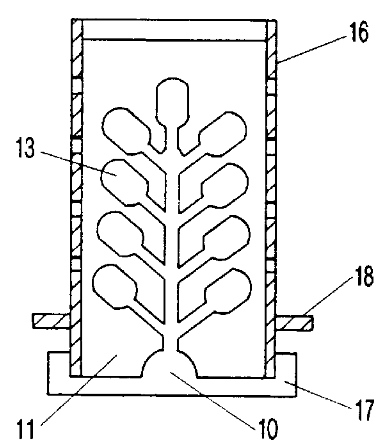
FIG. 1*e* is a side view of the structure in FIG. 1*d* after investment slurry has been poured into the flask.
Figure 2A:
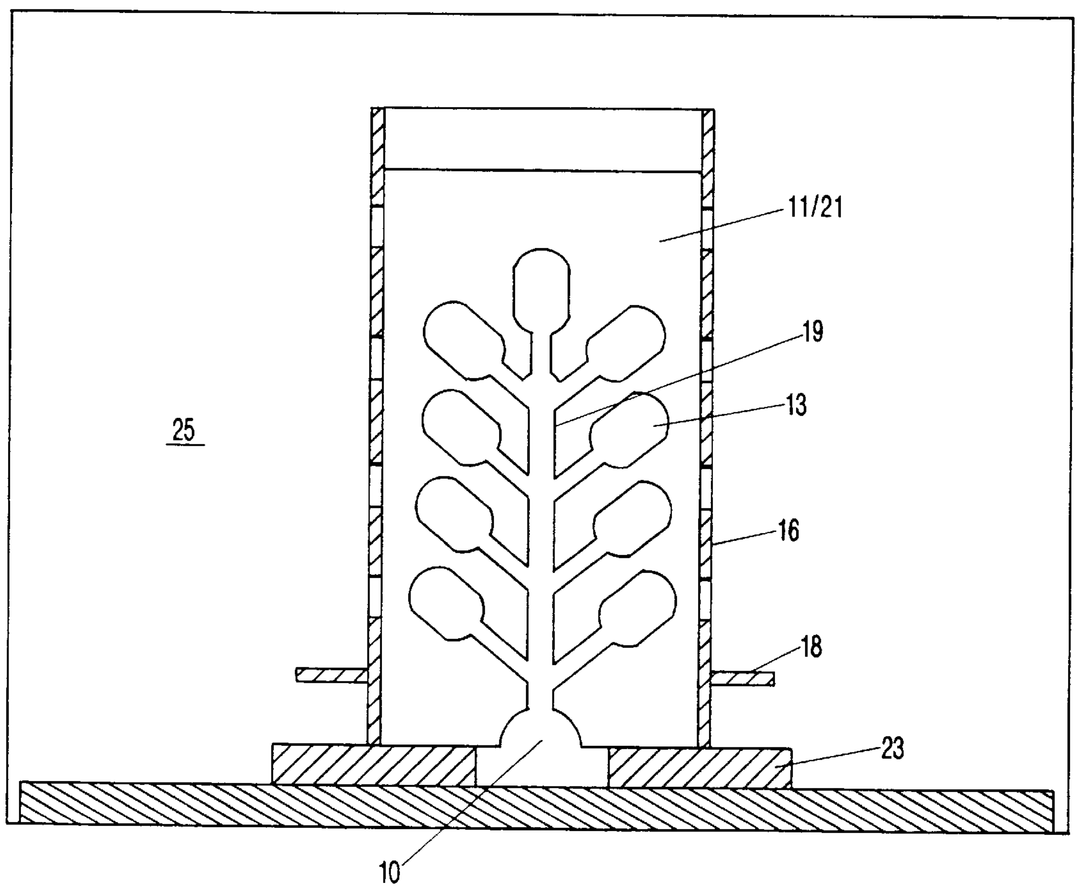
FIG. 2*a* is a side view of the structure of FIG. 1*e*, with the rubber base removed, elevated in a conventional oven or kiln.
Figure 2B:
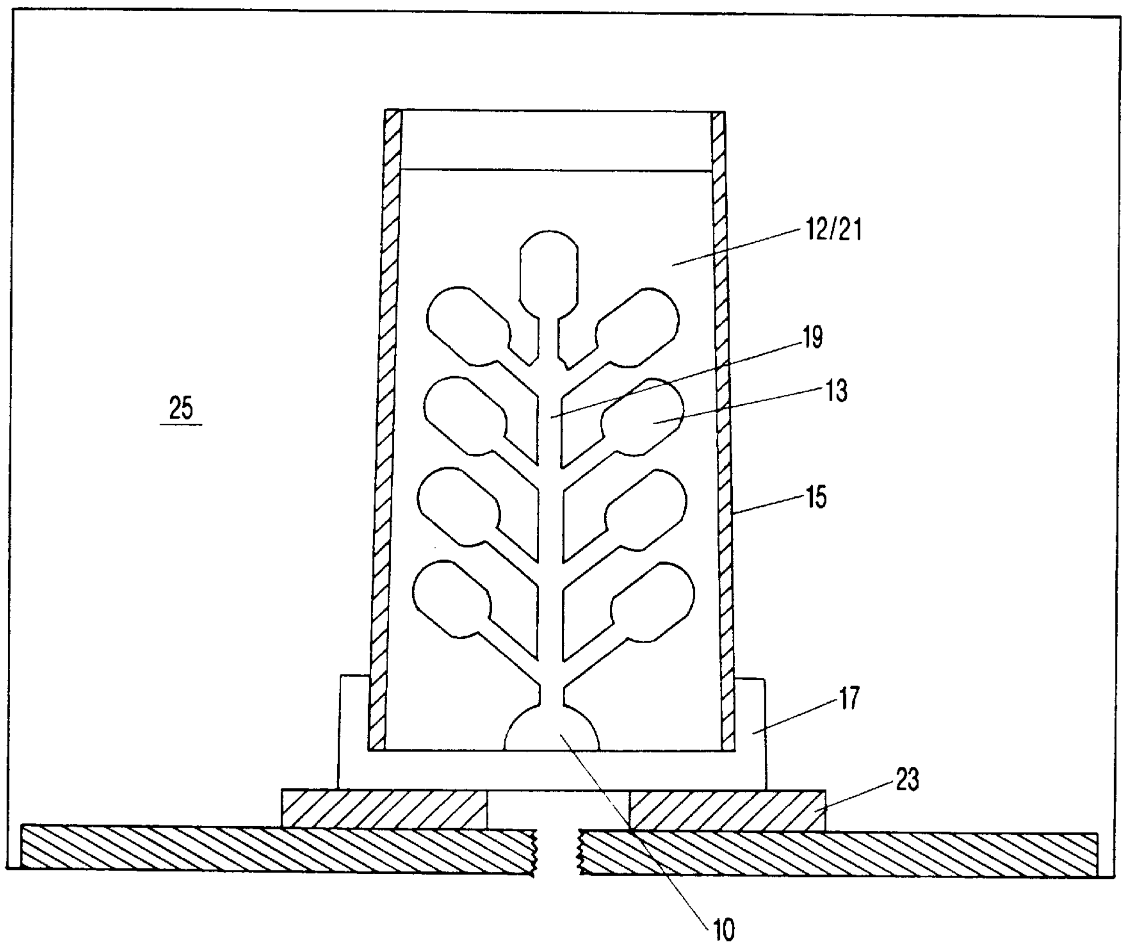
FIG. 2*b* is a side view of the structure of FIG. 1*c* elevated within a microwave oven cavity.
Figure 7:
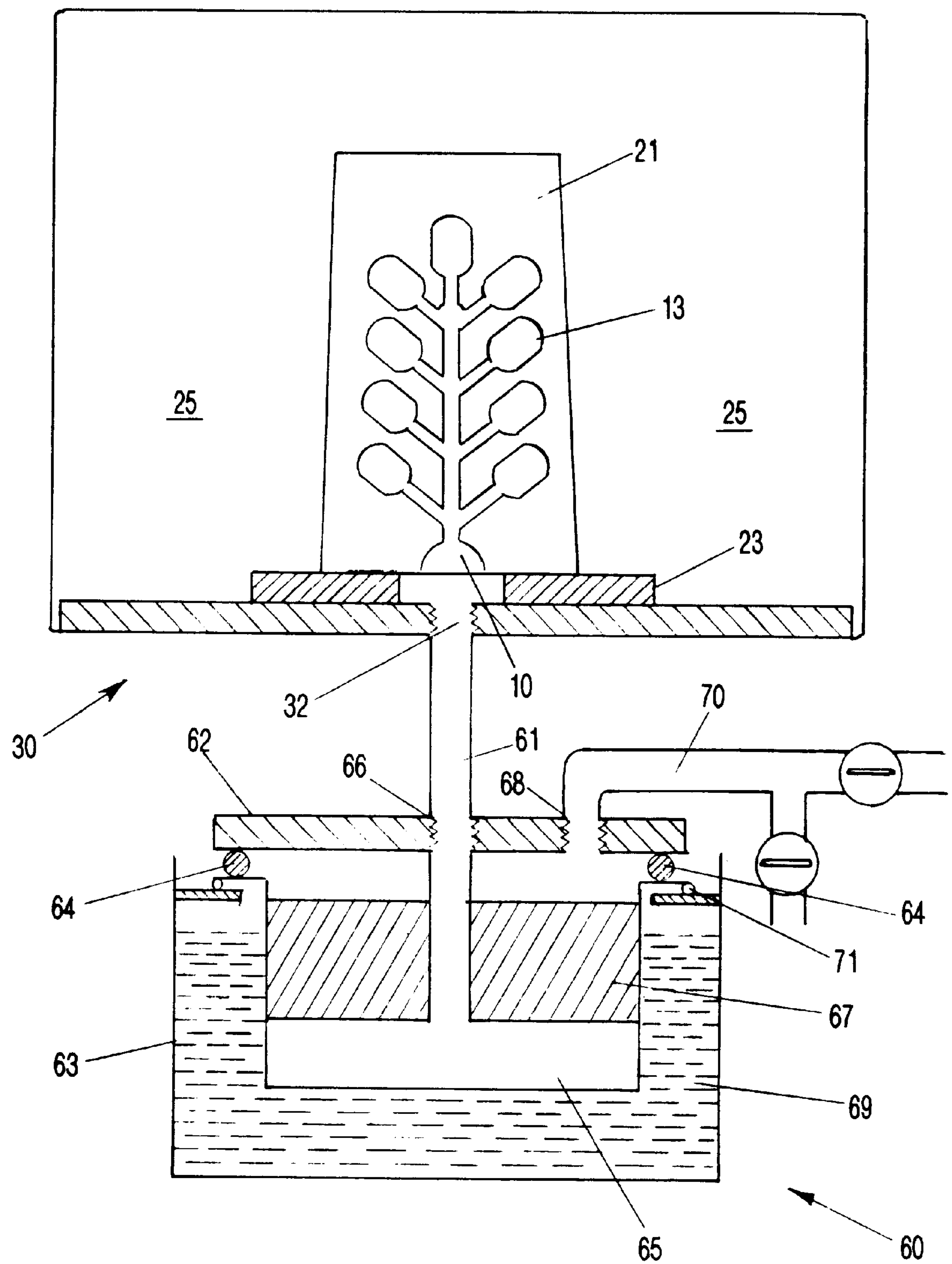
FIG. 7 is a side view of a mold within a microwave oven cavity, which is also attached to a vacuum apparatus.
Figure 8A:
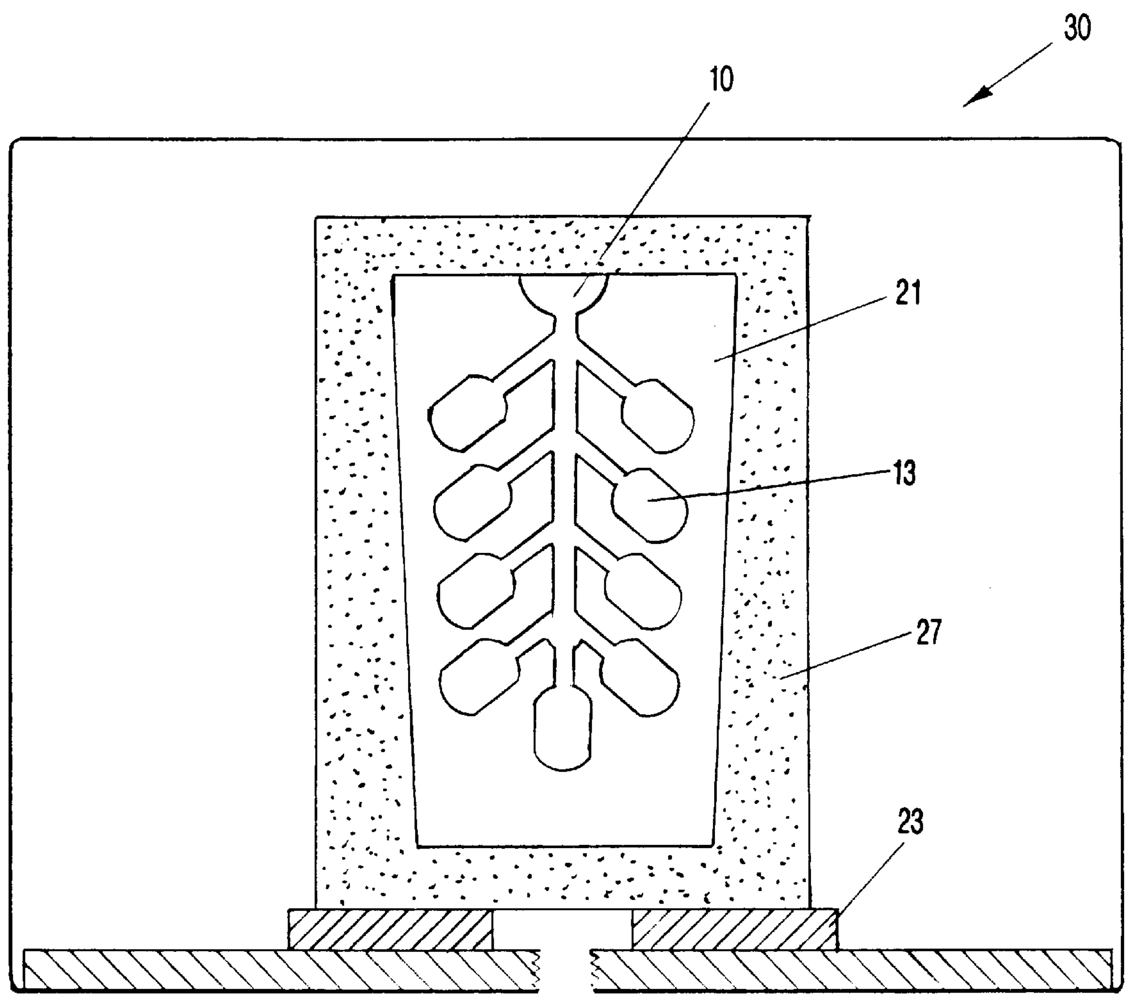
FIG. 8*a* is a side view of a mold encased within a heat shield within a microwave oven cavity.

Recalling FIG. 1a, 1b and 1c, the process of creating an oxidizing mold is similar to conventional mold making processes. Investment powder is mixed with at least one oxidizing agent and ordinary tap water to create an oxidizing slurry mixture. Wax tree 13 attached to rubber base 17 is then introduced into plastic or disposable flask 15, and the oxidizing slurry mixture is poured into flask 15 to completely encase wax tree 13. Because of the oxidizing agents in the mixture, the curing time of the mold will be notably reduced but will result in a rigid mold with wax tree 13 embedded therein. The mixture (12) can then be allowed to set fast in a hot air chamber or microwave (as shown in FIG. 2b) along with its sprue base 17. Once the mold has hardened flask (plastic or disposable) 15 and sprue base 17 are removed and the naked flaskless mold 21 can now be placed in a microwave oven 25 with its sprue hole 10 attached to a vacuum access as shown in FIG. 7. Sprue hole 10 of mold 21 should face downwards to allow wax tree 13 and other undesirable compounds to flow out. 98% of wax and 100% of the moisture will be eliminated in heating the mold as described. Finally, as the temperature is directly raised to a casting temperature of the metal (e.g. from 454°–676° C. (850°–1250° F.)), carbon is eliminated by 425° C. to 575° C. (800° F. to 1067° F.). When the temperature has been raised to casting temperature, as seen in FIG. 8a, sprue hole 10 should preferably face up as gases rise. Thus, unlike conventional methods, carbon is eliminated from the mold before the casting temperature is reached, dehydration and dewaxing of the mold is achieved simultaneously by either conventional or microwave heating and the casting temperature does not need to be exceeded.

Similarly, investment powders containing modifiers according to the present invention can incorporate what is defined as "special modifiers." In general, special modifiers are those chemicals or compounds which, when mixed with investment powder, react with compounds within the investment (such as oxygen) to form micropores, or air pockets, within the mold and thereby make the mold porous. Creation of micropores throughout the mold assists during vacuuming, for example, by creating paths for free vacuum flow. In this regard, undesired compounds contaminants and gases are vacuumed out of the mold throughout the mold. Additionally, molds containing micropores are easily broken apart when casting is completed, either by quenching the mold in water or by direct force. Special modifiers can be used with any form of investment powder, including those disclosed in the present invention, and can be carbonous or noncarbonous. The present invention's special modifiers are especially useful in molds which will be used for high temperature casting such as platinum casting, as such molds are required to be strong and concentrated due to the high heat temperatures dictated by these processes.

Sugar ($C_6H_{12}O_6$) is an especially useful special modifier. Sugar, in amounts ranging from 0.1% to 10%, dissolves and mixes well in investment slurry. At temperatures of 150–250° C. (302°–482° C.), sugar throughout the mold decomposes into fine particles of carbon. This excess carbon can then react with oxygen from the decomposed mold to provide micropores throughout the mold which will not affect the surface of the final casted metal. The creation of micropores also assists in easily disintegrating the mold after casting is completed, because as the mold is immersed in water, water enters the micropores of the hot mold to create vapor pressures which helps in breaking the mold apart.

The advantages to employing special modifiers, such as sugar, are numerous. First, these types of modifiers act as a retarder during the investment set up phase, thereby prolonging the amount of time to work with the slurry before it sets. Second, it is known to those in the art that wax floats on melted sugar. Therefore, molds doped with any special modifier should prevent some if not most wax from penetrating into the mold cavity surfaces when heat is applied and the wax thermally expands. This implies carbon of sugar ($C_6$) replaces some or most carbon of wax (paraffin range $C_{17}H_{36}$—$C_{35}H_{72}$) ($C_{17-35}$) in the mold cavities. Third, if a vacuum is applied to the mold, air pockets created by the carbon/oxygen reaction allows better vacuum flow of undesired compounds contaminants and gases from throughout the mold away from the mold cavity. Fourth, special modifiers decompose into a carbon component at a low temperature which allows the decomposed carbon to react with the mold's oxygen to form $CO_2$ and CO. If partial vacuum is applied, the $CO_2$ will be retrieved from the mold. Fifth, many special modifiers, including but not limited to sugar, have the unexpected benefit of also being susceptive to microwave energy.

Another advantage of employing special modifiers is that these modifiers react with and remove oxide from molten metal. As those skilled in the art understand, molten metal alloy usually contains some amount of oxygen. This oxygen could be introduced to the molten metal from a number of sources. For example, oxygen may be introduced when the molten metal is poured into the mold by getting oxidized in open air, or even from the mold itself. In some cases, this excess oxygen creates tiny pits in the metal known as porosity which results in surface flaws of the final cast product. In such cases, the final cast product must be reworked by hand to remove the flaws, or the cast product must be remelted for another casting attempt. Special modifiers, especially those special modifiers having a carbon component, react with the oxygen to form $CO_2$ and CO. If a vacuum is applied to the external surface of the mold corresponding to the air flow of any of the directions depicted in FIG. 5*g*, as the molten metal is cast, the existence of carbon dioxide in the mold will be extracted from the mold, resulting in a superior final cast product with little to no porosity.

If a very minute trace of carbon was present in the cavities of the mold, unlike the complete burn out of carbon, both carbon and CO acting as a reducing agent could help reduce metal oxides. Insufficient burn out could also result in incomplete castings which is true in the case of wax carbon, but experiments demonstrate that presence of a very small percentage of sugar carbon or wax carbon or both in the cavities of the mold yields good castings.

In another embodiment, the present invention includes the addition of modifiers/susceptors/special modifiers which exclude silica based compounds. The present invention replaces silica compounds with other chemical compounds. For example, and not by means of limitation, wollastonite can be mixed with gypsum to obtain a new investment powder for molds in casting metals. Preferably, a mixture of 10 to 70 percent wollastonite should be added with up to 30 to 90 percent of gypsum. Additionally, 30 to 60 percent of limestone ($CaCO_3$) can be added to the gypsum/wollastonite mixture as a filler. This combination of organic chemicals is non-silicate in nature, thereby resulting in extremely strong molds for naked or flaskless mold applications. Because the cured mold is strong, it is more resistant to thermal shocks, yet breaks apart easily when quenched in water. Additionally, unlike silica compounds, all components of this non-silica compound easily suscept to microwave energy. This form of powder is highly conductive, and molds produced with this powder are slightly porous which is an advantage when applying a vacuum to the mold. Finally, superior surface metal casting is achieved due to the fine mesh size of the individual chemical components. This new non-silica investment powder composition can replace traditional investment powder compositions and be utilized in the same manner. Consequently, oxidizing agents such as those disclosed in Table 2, can be admixed with the new non-silica investment powder to obtain the same benefits as previously described. Similarly, special modifiers, such as sugar, can be admixed with this investment composition to obtain benefits heretofore unknown in the art.

There are several factors that have to be taken into account in the making of a new investment powder. Parameters like working time, workability of the powder and the resulting surface of the casted metal are a few of the important ones.

Working time as described before is 8–9 minutes in case of a gypsum bonded investment powder, but is only 5–6 minutes in case of a phosphate bonded investment powder (which is especially formulated for higher melting temperature metal like platinum). Combinations of retarder and accelerator in very small percentages when added to gypsum bonded investment can give one the desired working time. However, using excessive percentages of retarder and accelerator with gypsum binders will show up as flaws in the final cast pieces. This could also be a guideline to follow for controlling the amount of retarder and accelerator in the new investment powder.

Workability of the new investment powder is to engineer the components of the powder in such a way that:

1. Right amount of water is used in obtaining a slurry which has good flowing properties for if an excessive amount of water is used, the final casting could turn out to be defective with water separation marks or water streak marks or the mold could crack during the process of heating or at the time of vacuum casting as the strength of the mold could be affected.
2. The slurry should vacuum easily so as to remove all the air bubbles from it, which are introduced in the slurry while mixing of the powder to the water takes place. Slurries that cannot be vacuumed good will yield defective castings with nodules.
3. No settling of particles (especially the heavy particles in the powder) takes place in the slurry once the flask is invested and is allowed to set (harden) undisturbed. The suspension of particles in the slurry is very important as the settling of particles by mere gravitational pull could cause defects like leave some added external imperfection on the underside of the final casting.

Figure 14:
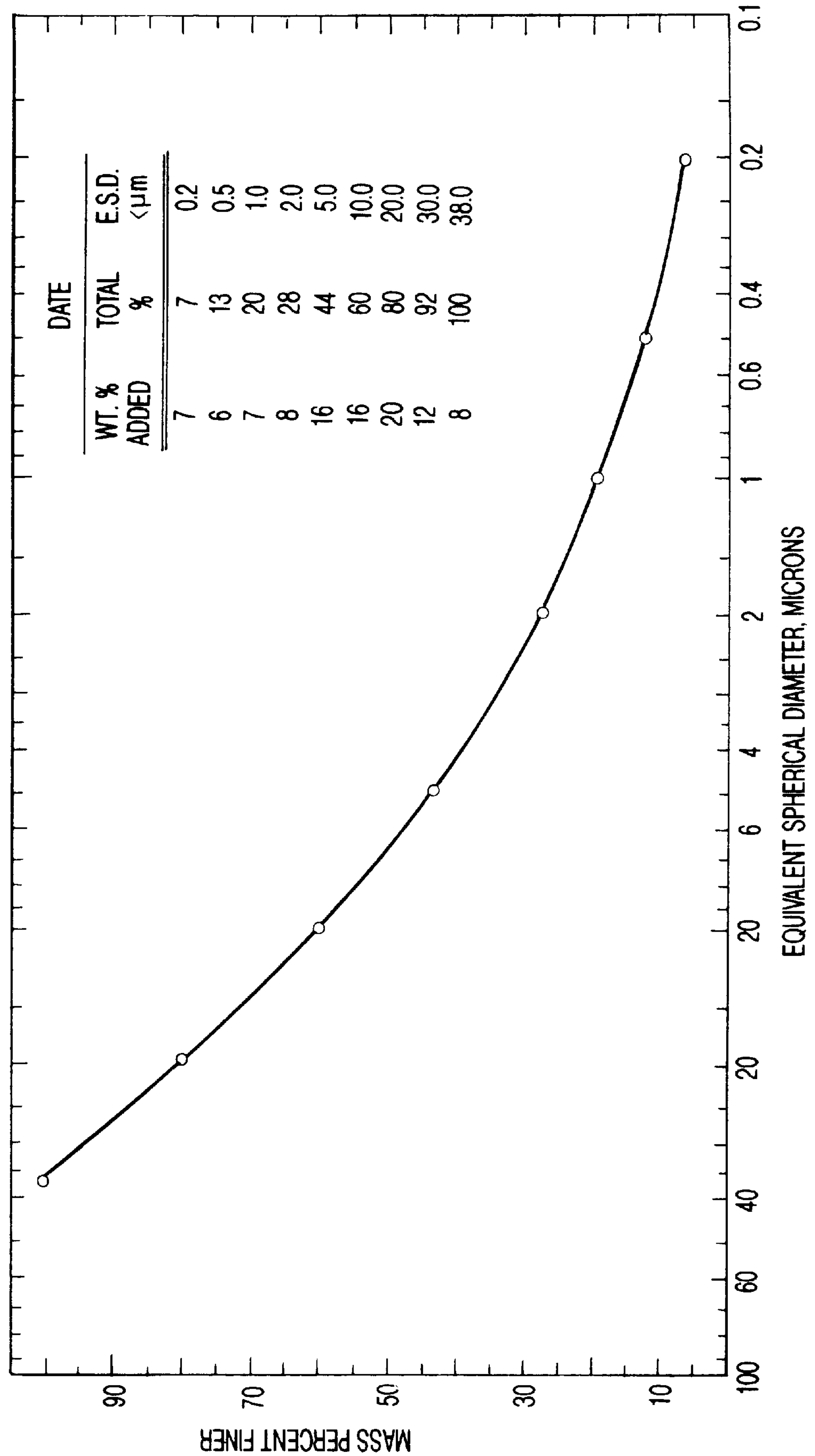
FIG. 14 particle size distribution for optimized packing of continuous particle size distribution.

Settling could be avoided by the following: (1) the particle distribution curve, FIG. 14, for each individual component in the investment powder or by obtaining a group mean curve close to FIG. 14 for all the components together in the powder; (2) the absorption properties of the individual components of the powder; or (3) the use of some commercial defloculating agents, like $NaCO_3$, etc. debubblizing and wetting agents are several in the market. Some dishwashing soap could also serve the purpose. Defloculents usually chemically charge the fine (lighter) particles in a clay slip (slurry). This creates a repulsion between these particles, helps suspending not only the lighter particles but interlocks other particles from settling (moving in the direction of the gravitational pull). Use of excessive amounts of fine particles in the powder could cause difficulties while vacuuming the slurry. Finally, the castings dictate the real solutions in the creation of the new investment powder, especially a flaw in the cast would reveal the culprit by repeating experiments in the trial and error method. This could also govern the restriction of use of chemicals with the investment powder that could either harm the metal while being casted in the cavities of the mold or deteriorate the mold.

EXAMPLE 5

To demonstrate the effect of 3% of $KNO_3$+1% of $CaNo_3$+1% SiC (600 mesh) on the properties of the gypsum binder (ST Georgia Pacific) when used with wollastonite (W-30 Venderbilt)

| New investment powder: | 65% gypsum (ST) | 520 gm |
|---|---|---|
| | 35% wollastonite (W-30) | 280 gm |
| | | 800 gm. |

Procedure (1) 800 gm of new investment powder is sufficient for making a 3½"×5" tapered flaskless mold (2) 800 gm ×0.38 =304 ml of $H_2O$ (38%) hot tap water about 110°–120° F. (43°–49° C.)

(3) 3% of $KNO_3$ (800 gm ×0.03 =24 gm of $KNO_3$) 1% of $Ca(NO_3)_2$ (800 gm ×0.01 =8 gm of $Ca(NO_3)_2$) 1% of SiC (600 mesh) (800 gm ×0.01 =8 gm of SiC)

(4) 1.67 gm of $NaCO_3$ (defloculent) was used 0.50 gm of debubblizer was used 0.015 gm of citric acid (dry) was used (5) Temperature of the water $+KNO_3+Ca(NO_3)_2+SiC$ $+NaCO_3+$ debubblizer+dry citric acid after it was well mixed for 1½ minutes was between 70°–80° F. (21°–27° C.).

(6) working time was 6–7 minutes setting time was 8½–10 minutes One styrofoam cup (12–16 oz.) with a small wax tree 3"–4" long on a 3½" sprue base was invested. Mold size 3½"×5" but tapered at the top end.

(7) Mold was allowed to set for 30–45 minutes at room temperature. Mold was very hard to fingernail pressure.

(8) Mold was removed from the styrofoam cup and the rubber sprue base and was placed in the microwave as in FIG. 7.

(a) 5 minutes under defrost cycle with vacuum at the mouth.

(b) 15–20 minutes under cook cycle with vacuum at the mouth. The mold is dewaxed and dehydrated by doing the above. Temperature of the mold at this point is about 200° C. (392° F.).

(c) Then the mold was placed in a heat shield and put back in the microwave oven as shown in FIG. 8*a*. for 15 minutes under cook cycle. By now the temperature of the cavity of the mold is around 600°–700° C. (1112°–1292° F.).

Mold temperature could be around 400°–500° C. (732°–932° F.). Reason: in microwave heating the interior of the mold gets hotter because of the exothermic reaction of carbon getting combusted by the oxygen released by the mold and hence produces more heat and may be because of the microwave susception of carbon particles in the cavity of the mold which could also produce extra heat. Repeated experiments were conducted with this kind of a mold at this stage when controlled by microwave hating (so as not to allow the temperature of the mold cavity to exceed far beyond the mold temperature) showed that the carbon was eliminated completely from the cavity by 425° C. (797° F.).

The mold was allowed to cool (actually the cavity of the mold) for 10–15 minutes until it comes down to 500° C. (932° F.) for casting purposes.

Figure 8B:
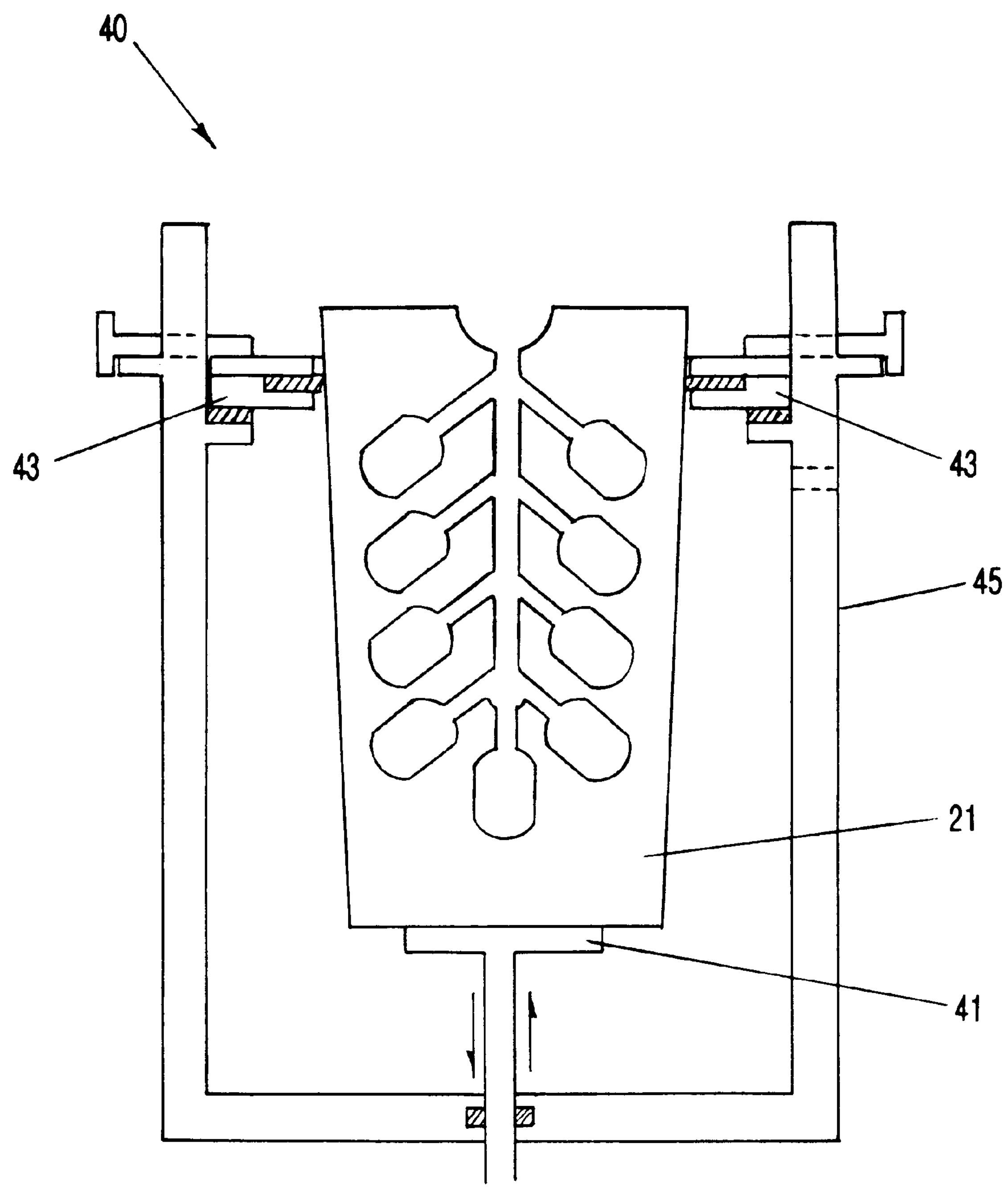
FIG. 8*b* is a side view of a flaskless tapered mold being vacuumed all around except the mouth (as described in FIG. 6*g*) in a vacuum casting chamber just before pouring molten metal for casting.

300 gm. of sterling silver was cast in this flaskless mold as in FIG. 8*b*.

(9) Results very good cast with very slight surface imperfections only on the underside of the castings.

(10) Observations

Hard mold, no cracks, needs hammering to break the mold.

Excellent elimination of carbon.

Cast pieces have bright satin surface imperfections on the underside of castings due to particle mesh size of the investment powder.

(11) Conclusion

New investment powder is strong enough for being flaskless molds, but doesn't break away well just by quenching in water.

Figure 6:
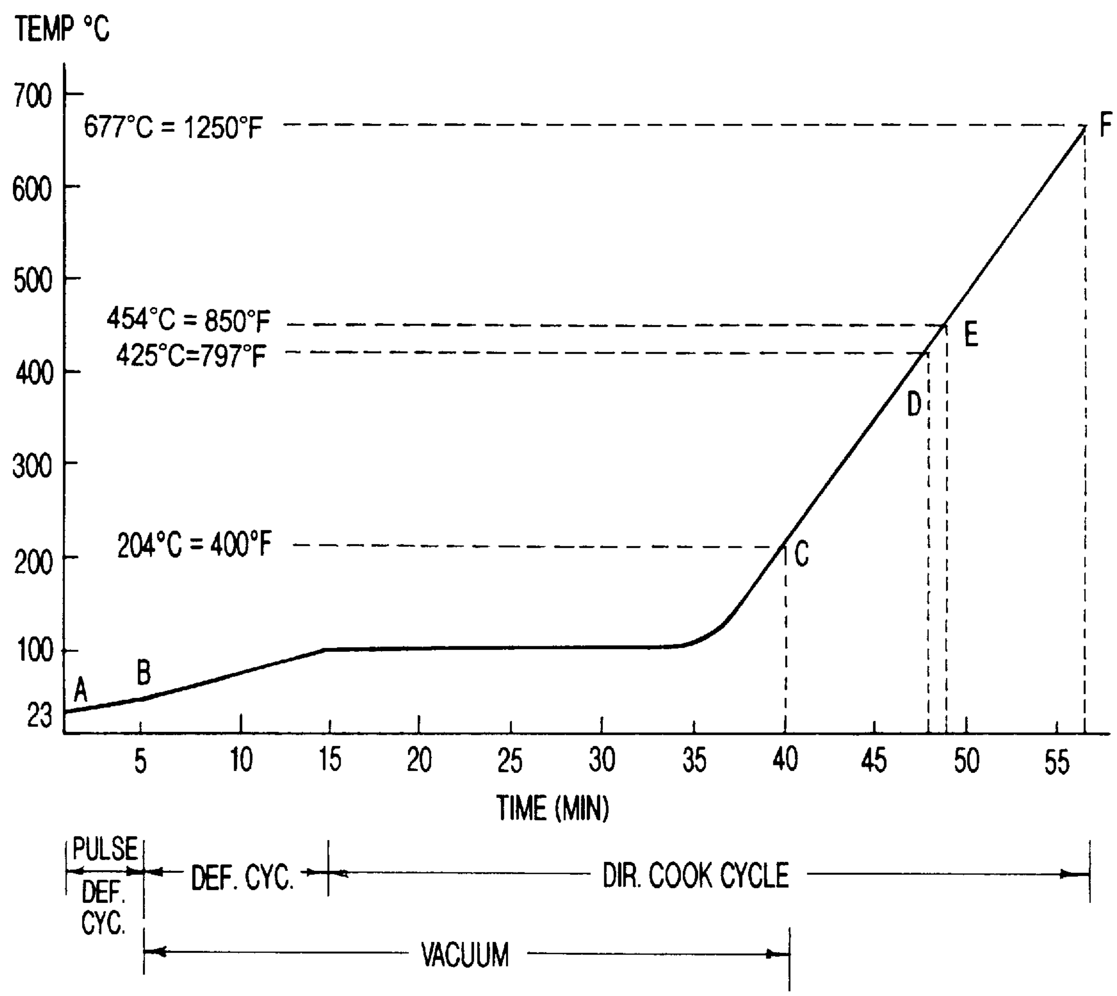
FIG. 6 is a time versus temperature graph when an investment mold with suscepting agents is prepared according to the present invention and heated with microwave energy.

Another embodiment of the present invention includes the addition of suscepting agents to conventional investment powders or the powders disclosed herein. Suscepting agents, or "susceptors," are compounds whose molecules are excited when subjected to microwave energy. As these molecules are excited, heat energy is created. When susceptors are mixed with investment powder, the resulting mold can be rapidly heated in a microwave oven, and further allow a foundry operator or caster to maintain and stabilize the temperature within the mold at a predetermined level. As seen in FIG. 6, molds containing susceptors can be set in 5–15 minutes, complete the dehydration and dewaxing of the mold in 35 minutes, and can achieve carbon burn out in less than 1 hour. Again, as noted previously, because carbon burn out takes place at a much lower temperature (e.g., 425° C. (797° F.) and up), the temperature of the mold can then be directly raised to a casting temperature. Processing time employing the present invention, therefore, is a fraction of the time needed to complete the same process under conventional methods. Preferably, 0.1 to 6 percent of $KNO_3$, 0.1 to 8 percent of $CaNO_3$ or 0.1 to 10 percent of sugar can be used as suscepting agents. Additionally, up to 10 percent of SiC can be further mixed with investment to form a "susceptible mold." Other acceptable susceptors include water and carbon and those compounds listed in Table 2. As those skilled in the art can appreciate, any combination of susceptors may be admixed with conventional investment powders or with the investment powders disclosed herein to obtain the benefits described.

Figure 11:
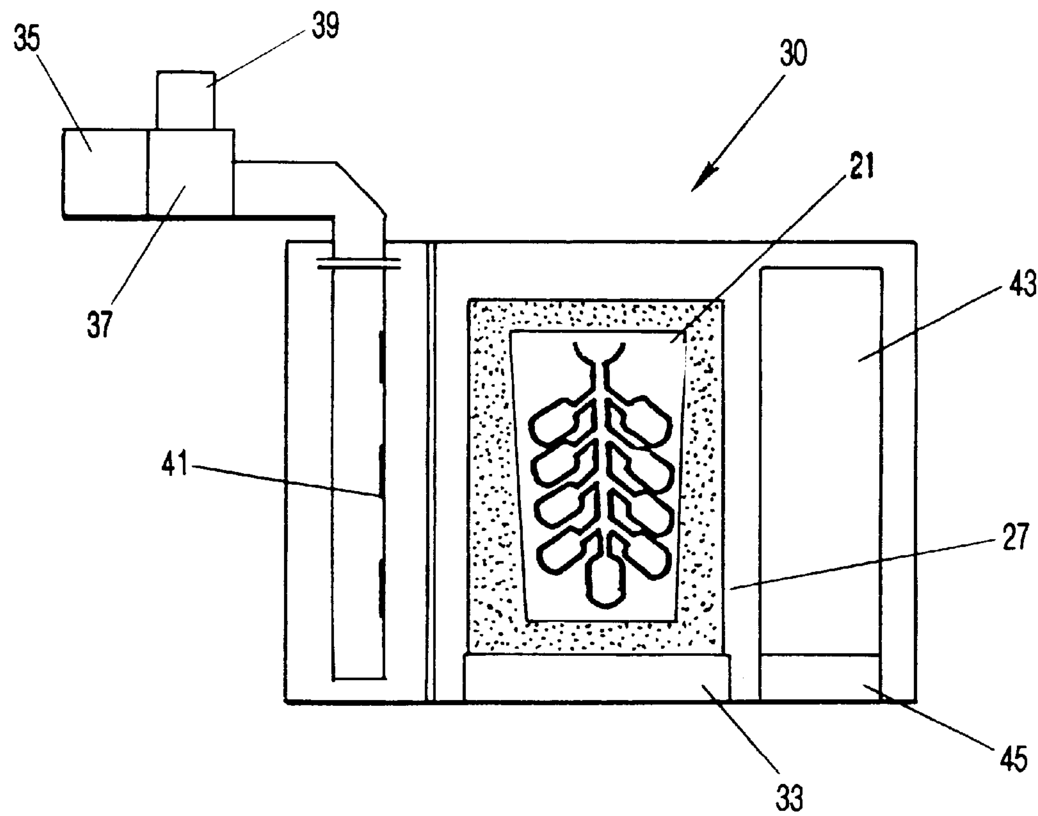
FIG. 11 is a side view of a mold within a microwave oven for uniformly heating a mold.
Figure 12:
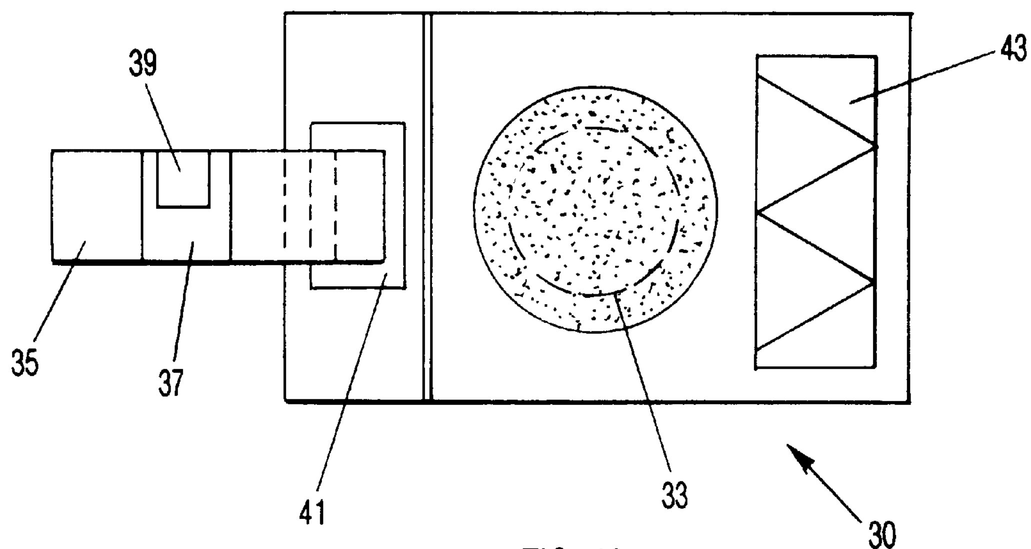
FIG. 12 is a top view of FIG. 11.
Figure 13A:
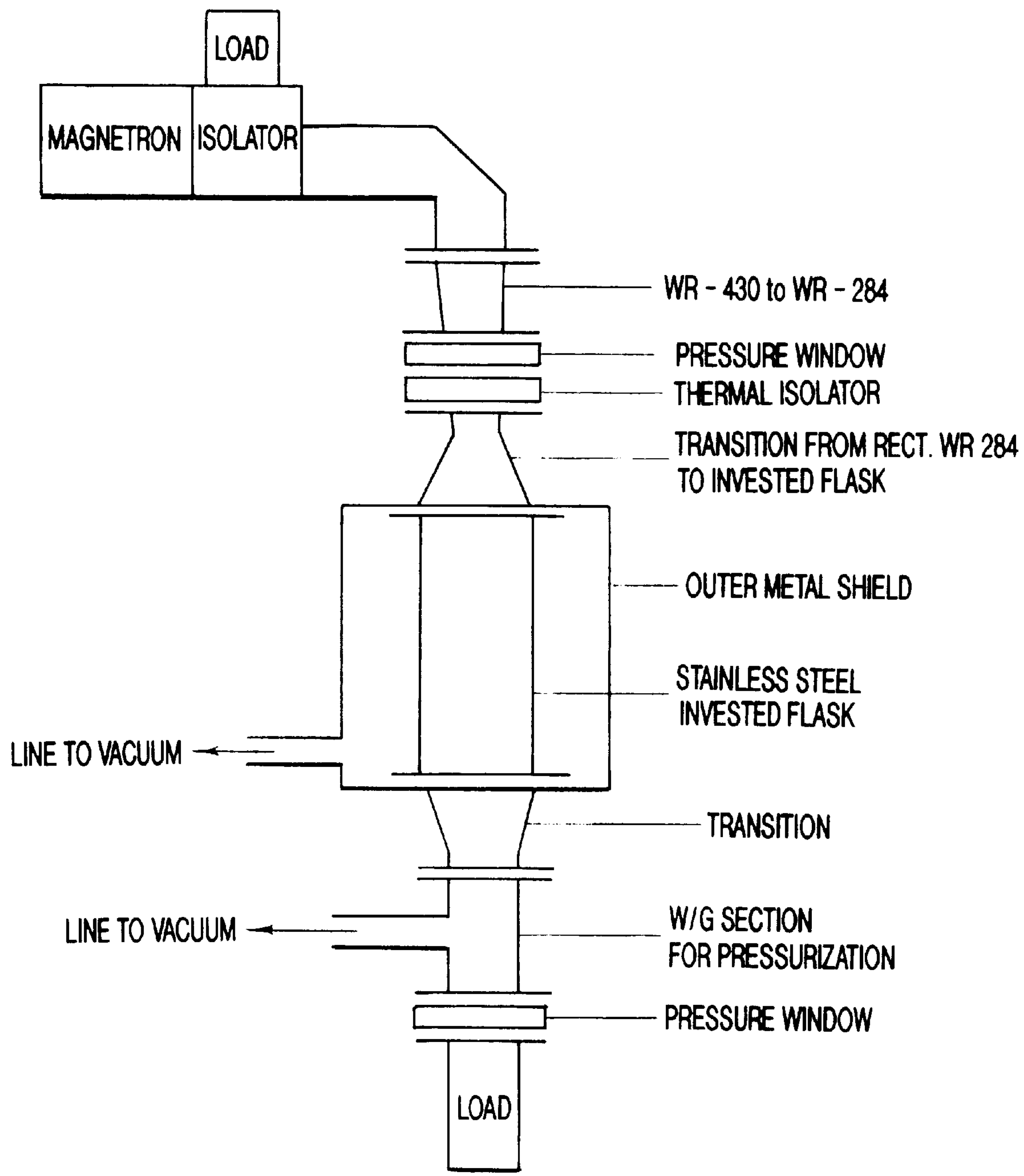
FIG. 13*a* is a side view of an optional microwave oven wherein an invested metal flask is an extension of a microwave guide.
Figure 13B:
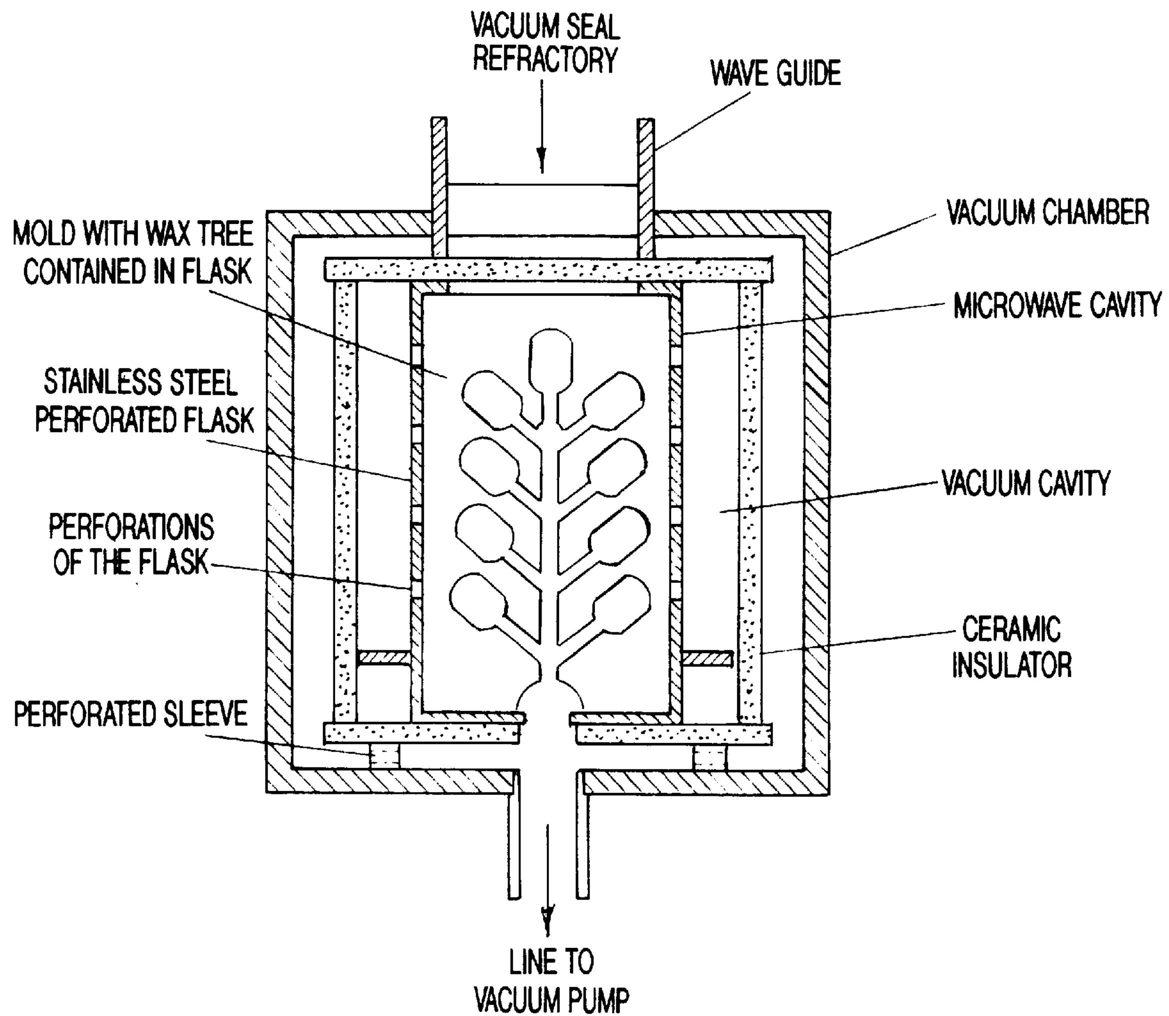
FIG. 13*b* is a cross-sectional view of the microwave oven of FIG. 13*a*.

Like oxidizing molds, the advantages of a susceptible mold are extensive. First, susceptor agents contribute to the rapid setting of the mold. Second, carbon is eliminated due to the reaction of oxygen from the modifier with carbon particles from the (oxidizing agent) with carbon particles to form $CO_2$ and CO. Third, because of the nature of microwave energy and the use of susceptors dispersed throughout the mold, uniform heating can occur throughout the mold. If the mold is rotated within the microwave, as seen in FIG. 11, uniform heating will be achieved throughout the mold. Fourth, as seen in FIG. 6, use of susceptors results in significant time and energy savings over conventional casting methods. Finally, use of a suscepting mold allows for casting with gemstones at lower temperatures than conventionally used without harm to the gemstones.

Figure 9:
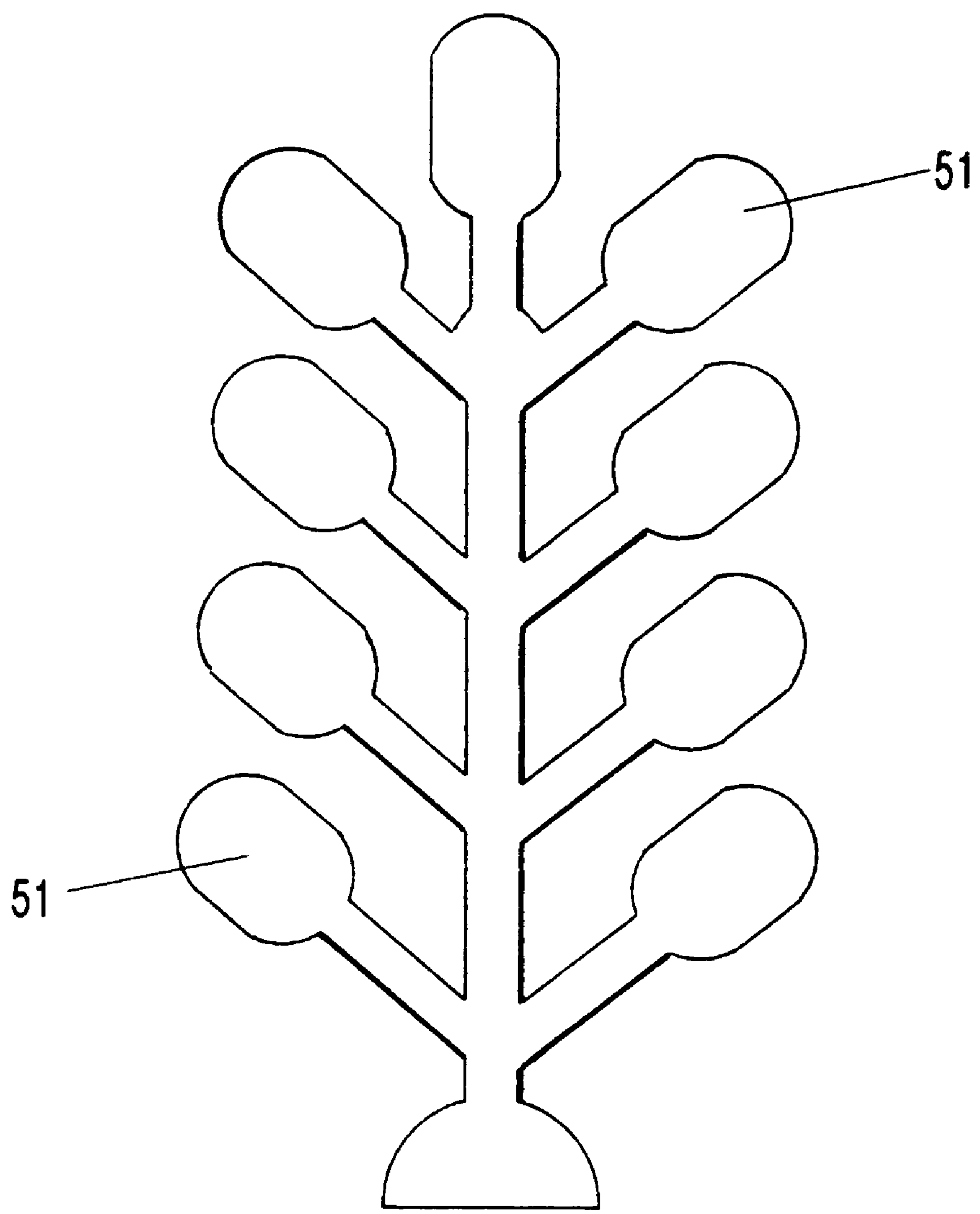
FIG. 9 is a side view of a final cast metal product.

Again, recalling FIGS. 1*a*, 1*b* and 1*c*, the process of creating a susceptor mold is similar to conventional mold making processes. Investment powder is mixed with suscepting agents to create a suscepting mixture. The resulting mixture is then poured into flask 15 containing wax tree 13 and the mixture is allowed to set undisturbed in microwave 25 (FIG. 2*b*). The mixture can then be cured in a microwave oven cavity (shown, for example, as 25 in FIG. 7) while wax tree 13 is dewaxed, thereby eliminating 98 percent of the wax and 100 percent of the moisture. Some plastics don't melt. Molds with such plastic patterns are just dehydrated in the same way. Both plastics that melt or don't melt burn and vaporize completely in the final stages. Plastics normally vaporize at 538° C. (1000° F.), unlike wax which vaporizes at 732° C. (1350° F.) in the conventional heating way. Preferably, sprue hole 10 of mold 21 should face downwards to allow the wax and other undesirable compounds to flow out. Finally, as the mold temperature is directly raised to a casting temperature from 454°–676° C. (850°–1250° F.) in the microwave oven, carbon is eliminated above 425° C. (797° F.). Of course, as seen in FIG. 11*a*, those skilled in the art will realize that multiple molds may be placed in a microwave oven cavity for processing. When the mold temperature is raised to a casting temperature, as seen in FIG. 8*a*, sprue hole 10 should preferably face up as gases rise. Because the mold must rapidly achieve high temperatures, mold 21 should be encased in a heat shield 27, such as a thermal blanket, to prevent heat from radiating away and from absorbing the ambient temperature around which could cause cracks in the mold due to uneven heat inside to outside of the mold. When the casting is complete, mold 21 is broken or disintegrated by any conventional method, and final cast metal product 51, as seen in FIG. 9, is retrieved.

Figure 10A:
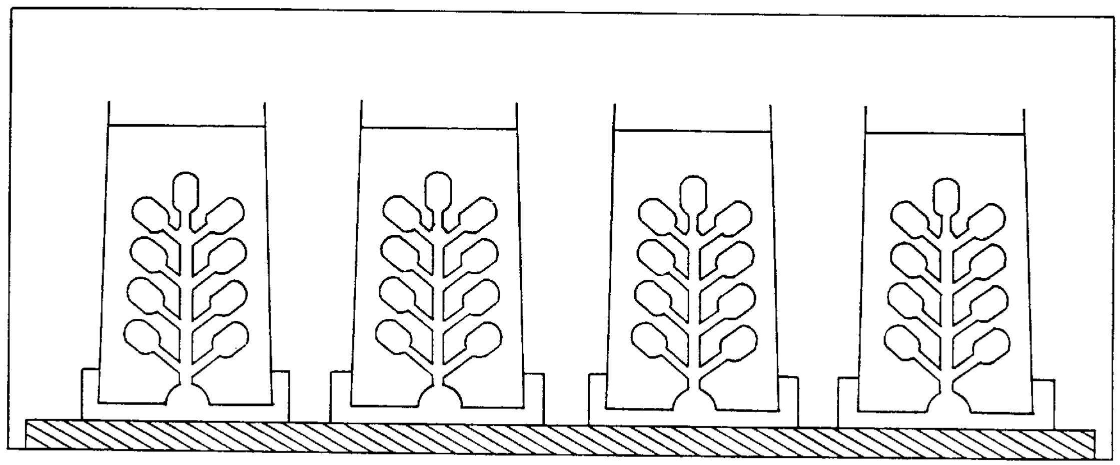
FIG. 10*a* is a side view depicting multiple molds with sprue bases, within an oven (microwave or hot chamber) cavity for setting such molds.
Figure 10B:
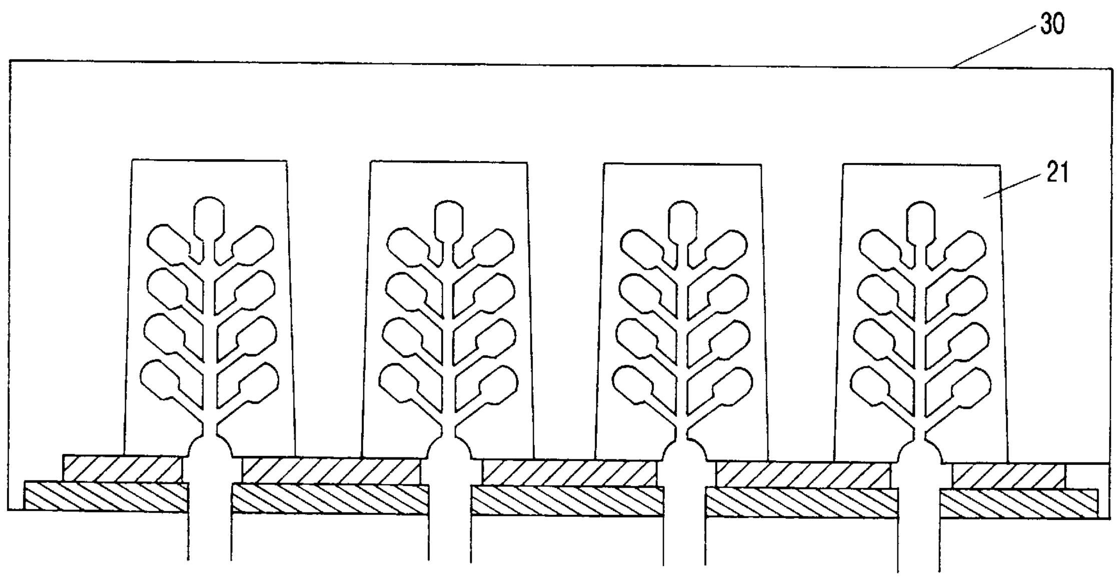
FIG. 10*b* is a side view depicting multiple molds within a microwave oven cavity attached to multiple vacuum systems for dewaxing and dehydrating.

Additionally, as shown in FIG. 7, optional vacuum system 60 can be directly attached to an opening 32 of microwave oven 30 to assist in the dehydration, dewaxing and carbon elimination processes. Vacuum system 60 includes vacuum flow tube 61 directly attached to microwave oven 25 at opening 32. System 60 further includes stainless steel container 63 having cavity 65 which functions as a depository for melted wax retrieved from mold 21. Vacuum system 60 further includes filter 67 for filtration of water and wax from entering into external vacuum pump line 70 and an interior coolant channel 69 filled with cool water to assist in the cooling of the deposited melted wax from mold 21. System 60 incorporates lid 62 which is attached pressure-tight to container 63 by vacuum seal 64. Lid 62 further includes opening 66 to securely receive vacuum flow tube 61, and opening 68 to securely receive external vacuum pump line 70. Of course, those skilled in the art will appreciate that multiple vacuum systems 60 can be directly attached to oven 25 to assist in the elimination of water, wax and (optionally) carbon. As such, as seen in FIG. 10*b*, multiple vacuum pressures can be applied to or from any point on the exterior wall of mold 21 within oven 25.

Optionally, as seen in FIG. 11, microwave oven 30 can incorporate rotatable pedestal 33. In this oven configuration, oven 30 further includes a conventional magnetron 35, isolator 37, load 39, along with slotted wave guide and array antenna 41 located on a side wall of oven 30, a reflector 43 disposed atop foam pedestal 45 located on another side wall of oven 30. In this configuration, mold 21 is placed upon rotatable pedestal 33 and microwave energy is applied by conventional use of magnetron 35, load 39 and isolator 37. As microwave energy is applied, microwave energy is ricocheted off the oven's interior wall surfaces and off reflector 43 onto mold 21 as it rotates and therefore, uniform heating is achieved throughout mold 21. Of course, heat shield 23 can also be applied to an external surface of mold 21 to prevent heat generated by mold 21 from radiating away, and from absorbing the cold from the ambient temperature which could cause cracks in the mold.

Finally, because of the thermal expansion of wax, it is advisable to dewax the mold before dehydration of the mold begins. Therefore, it is preferred to start melting the wax prior to dewaxing the mold in the oven. This can be accomplished by heating a syringe needle attached to a syringe, for example and piercing the wax tree through its sprue rod. Preferably, the syringe needle should have multiple orifices for maximum extraction of melted wax. If possible, the syringe handle should be conventionally engaged as it enters the wax tree sprue rod in order to extract the melted wax. In this fashion, a portion of the sprue rod wax will initially be removed prior to dewaxing and dehydrating the mold.

EXAMPLE 6

For a 4 inch diameter by 8 inch high mold, a wax tree with wax patterns to be cast is attached to a rubber sprue base making sure that there is a gap of at least ¼ inch between the wax tree and the wall of the flask. Conventional investment powder is admixed with 1–10 percent SiC 80–800 mesh, 0–6 percent $KNO_3$, 0–8 percent $CaNO_3$ and 0–10 percent sugar. The resulting slurry is then poured into the plastic flask which has the wax tree on a sprue based, making sure that the slurry covers at least ½ inch above the top of the tree and is vacuumed twice for a total of 2½ to 3 minutes to eliminate air from the slurry. Microwave heat from a 0.750 KVA oven is then applied to the slurry to accelerate the set up time. The hardened mold is then removed from the flask and the rubber sprue base is pulled from the mouth of the mold. The naked mold is then placed in the microwave oven with its mouth facing down and sealed to the vacuum access. Low power microwave heating is applied for approximately ten minutes to avoid cracking due to vapor pressure. Higher powered microwave heating can then be applied for another 25 minutes, thereby eliminating 98 percent of the wax and 100 percent of water. In our experiments, the temperature of the mold is now approximately 400° F. (240° C.). Next, the mold can be enclosed in a heat shield and with its mouth facing up, be subjected to additional microwave heating for approximately 15 minutes. During this time, carbon is eliminated by combining oxygen generated from the mold composition at approximately 425° C. (797° F.) and up and the temperature of the mold rises rapidly to the casting temperature range of 850°–1250° F. (454° C.–677° C.). FIG. 6 graphically depicts the experimental results, wherein identifier A is the point where the mold is poured into a flask, identifier B denotes the point where the mold is set, hardened enough to take a vacuum pull and is removed from the plastic flask and the rubber sprue base. A 4×8 mold could take 5–15 minutes for setting (hardening) when 5 minutes is the microwave time and 10 minutes is the intermediate intervals of starting and stopping of microwaves, C denotes the elimination of water and wax, D denotes the point where most of the carbon is eliminated and identifiers E through F denote raising the mold temperature directly to the casting temperature range of the mold. As can be seen, total processing time from start to achieving casting temperature range is 55 minutes.

It is preferable that the modifiers (e.g., oxidizing agents and special modifiers) not only allow the mixture to be heat conductive, they should also preferably suscept to microwave energy. In this fashion, not only do the modifying agents work rapidly in conventional heating methods, they are also susceptible to other forms of energy which can produce heat within the mold.

Whereas the drawings and accompanying description have shown and described the preferred embodiment of the present invention, it should be apparent to those skilled in the art that various changes may be made in the form of the invention without affecting the scope thereof.

We claim:

1. An improved investment powder for use in making molds for casting metals at a selected mold casing temperature range, said temperature range being no greater than casting temperature of the metal being cast, said powder including gypsum and, at least, one form of silica, said powder being improved by the use of at least one water soluble oxidizing agent selected from the group consisting of $KNO_3$, $Ca(NO_3)_2$, $LiNO_3$, Fe $(NO_3)_2$, $NaNO_2$, $Ni(NO_3)_2$, $Cu(NO_3)_2$, $Al(NO_3)_2$, $NH_4NO_3$ and Mg $(NO_3)_2$ and present at ½–10% of said powder, where, when heated, said oxidizing agent releases oxygen at temperatures below said selected mold casting temperature range and said release of oxygen allows elimination of water wax and residual carbon present in said mold at said temperature range.

2. The investment powder as set forth in claim 1, wherein said at least one oxidizing agent $KNO_3$, and said $KNO_3$ comprises ½–3% of said powder.

3. The investment powder as set forth in claim 1, wherein said at least one oxidizing agent is $Ca(NO_3)_2$, and said $Ca(NO_3)_2$ comprises approximately ½–2½% of said powder.

4. The investment powder as set forth in claim 1, further including 1 to 10% of glucose, wherein said glucose decomposes to carbon below said selected mold casting temperature range.

5. The investment powder of claim 1, further including up to 10% SiC.

6. The investment powder as set forth in claim 1 wherein wollastonite replaces said silica.

7. The investment powder as set forth in claim 6, wherein said gypsum comprises between approximately 30 and 90% of said powder, and said wollastonite comprises between approximately 10 and 70% of said powder.

8. The investment powder as set forth in claim 6, further including between 1 and 10% glucose wherein said glucose decomposes to carbon below said selected mold casting temperature range.

9. The investment powder as set forth in claim 6, wherein said at least one oxidizing agent are $KNO_3$ and $Ca(NO_3)_2$, wherein said $KNO_3$ and $Ca(NO_3)_2$ each comprises between ½–10% of said powder.

10. The investment powder as set forth in claim 6, further including up to 10% SiC.

11. An improved investment powder for use in making molds for casting metals, said powder including gypsum, and, at least, one form of silica, said powder being improved by the use of 0.1–10% glucose, wherein said glucose decomposes to carbon below a selected mold casting temperature range, said temperature range being no greater than the casting temperature of the metal being cast, wherein said decomposition renders said molds more susceptible to heat radiation.

* * * * *